US 9,250,106 B2

(12) United States Patent
Rosinko et al.

(10) Patent No.: US 9,250,106 B2
(45) Date of Patent: *Feb. 2, 2016

(54) METHODS AND DEVICES FOR DETERMINATION OF FLOW RESERVOIR VOLUME

(71) Applicant: Tandem Diabetes Care, Inc., San Diego, CA (US)

(72) Inventors: Michael J Rosinko, Anaheim, CA (US); Paul M. DiPerna, Cardiff by the Sea, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 132 days.

This patent is subject to a terminal disclaimer.

(21) Appl. No.: 14/070,879

(22) Filed: Nov. 4, 2013

(65) Prior Publication Data

US 2015/0122052 A1    May 7, 2015

Related U.S. Application Data

(63) Continuation of application No. 12/714,299, filed on Feb. 26, 2010, now Pat. No. 8,573,027.

(60) Provisional application No. 61/156,405, filed on Feb. 27, 2009, provisional application No. 61/184,282, filed on Jun. 4, 2009.

(51) Int. Cl.
*G01F 1/34* (2006.01)

(52) U.S. Cl.
CPC ........................................ *G01F 1/34* (2013.01)

(58) Field of Classification Search
CPC ............ G01F 1/34; G01N 3/02; B25B 23/14; G01P 21/00; A61M 5/30

USPC ............ 73/861.42, 1.36, 856, 862.21; 604/66
See application file for complete search history.

(56) References Cited

U.S. PATENT DOCUMENTS

| 3,123,900 A | 3/1964 | Millar |
| 3,493,496 A | 2/1970 | Bray et al. |
| 3,648,694 A | 3/1972 | Mogos et al. |
| 3,665,967 A | 5/1972 | Kachnik |
| 3,699,812 A | 10/1972 | Masnik |
| 3,756,459 A | 9/1973 | Bannister et al. |

(Continued)

FOREIGN PATENT DOCUMENTS

| EP | 272530 B1 | 10/1991 |
| EP | 560571 B1 | 5/1997 |

(Continued)

OTHER PUBLICATIONS

Application and File History for U.S. Appl. No. 12/260,804, filed Oct. 29, 2008, inventor DiPerna.

(Continued)

*Primary Examiner* — Jewel V Thompson
(74) *Attorney, Agent, or Firm* — Patterson Thuente Pederson, P.A.

(57) ABSTRACT

A novel enhanced flow metering device is adapted for disposing into a flow material reservoir a known volume of flow material whereby software used in conjunction with a pressure sensor may be calibrated. Additionally, by measuring the known amount of flow material returning to the flow material reservoir, checks are quickly made to ensure the pressure sensor is behaving as expected.

17 Claims, 13 Drawing Sheets

(56) References Cited

U.S. PATENT DOCUMENTS

| | | | |
|---|---|---|---|
| 3,845,259 A * | 10/1974 | Spurr | 200/81.9 R |
| RE28,890 E | 7/1976 | Ingram et al. | |
| 4,184,342 A | 1/1980 | Pohl | |
| 4,265,241 A | 5/1981 | Portner et al. | |
| 4,314,797 A | 2/1982 | Gerwin | |
| 4,314,979 A | 2/1982 | Deabriges | |
| 4,330,071 A | 5/1982 | Ohlson | |
| 4,364,413 A | 12/1982 | Bersin et al. | |
| 4,469,481 A | 9/1984 | Kobayashi | |
| 4,520,948 A | 6/1985 | Hampel et al. | |
| 4,529,401 A | 7/1985 | Leslie et al. | |
| 4,559,038 A | 12/1985 | Berg et al. | |
| 4,565,542 A | 1/1986 | Berg | |
| 4,636,226 A | 1/1987 | Canfora | |
| 4,650,469 A | 3/1987 | Berg et al. | |
| 4,673,415 A | 6/1987 | Stanford | |
| 4,684,367 A | 8/1987 | Schaffer et al. | |
| 4,823,844 A | 4/1989 | Bartholomew | |
| 4,897,906 A | 2/1990 | Bartholomew | |
| 4,936,832 A | 6/1990 | Vaillancourt | |
| 4,969,884 A | 11/1990 | Yum | |
| 4,985,015 A | 1/1991 | Obermann et al. | |
| 4,989,456 A | 2/1991 | Stupecky | |
| 5,011,477 A | 4/1991 | Winchell et al. | |
| 5,038,821 A | 8/1991 | Maget | |
| 5,044,900 A | 9/1991 | Cavallaro | |
| 5,084,021 A | 1/1992 | Baldwin | |
| 5,091,094 A | 2/1992 | Veech | |
| 5,135,491 A | 8/1992 | Baldwin | |
| 5,135,498 A | 8/1992 | Kam et al. | |
| 5,135,499 A | 8/1992 | Tafani et al. | |
| 5,167,633 A | 12/1992 | Mann et al. | |
| 5,176,644 A | 1/1993 | Srisathapat et al. | |
| 5,186,431 A | 2/1993 | Tamari | |
| 5,197,322 A | 3/1993 | Indravudh | |
| 5,207,642 A | 5/1993 | Orkin et al. | |
| 5,207,666 A | 5/1993 | Idriss et al. | |
| 5,217,422 A | 6/1993 | Davis | |
| 5,241,935 A | 9/1993 | Beck et al. | |
| 5,247,434 A | 9/1993 | Peterson et al. | |
| 5,257,971 A | 11/1993 | Lord et al. | |
| 5,272,909 A | 12/1993 | Nguyen et al. | |
| 5,308,340 A | 5/1994 | Harris | |
| 5,316,261 A | 5/1994 | Stoner | |
| 5,326,468 A | 7/1994 | Cox | |
| 5,334,162 A | 8/1994 | Harris | |
| 5,335,852 A | 8/1994 | Muntean et al. | |
| 5,336,051 A | 8/1994 | Tamari | |
| 5,341,783 A | 8/1994 | Beck et al. | |
| 5,342,305 A | 8/1994 | Shonk | |
| 5,349,933 A | 9/1994 | Hasegawa et al. | |
| 5,366,904 A | 11/1994 | Qureshi et al. | |
| 5,367,910 A | 11/1994 | Woodward | |
| 5,369,976 A | 12/1994 | Ratton | |
| 5,388,453 A | 2/1995 | Ratton et al. | |
| 5,425,374 A | 6/1995 | Ueda et al. | |
| 5,429,483 A | 7/1995 | Tamari | |
| 5,433,710 A | 7/1995 | Vanantwerp et al. | |
| 5,435,465 A | 7/1995 | El Amin | |
| 5,441,027 A | 8/1995 | Buchanon et al. | |
| 5,448,978 A | 9/1995 | Hasegawa et al. | |
| 5,460,030 A | 10/1995 | Bloxsom et al. | |
| 5,462,525 A | 10/1995 | Srisathapat et al. | |
| 5,466,218 A | 11/1995 | Srisathapat et al. | |
| 5,472,577 A | 12/1995 | Porter et al. | |
| 5,476,449 A | 12/1995 | Richmond | |
| 5,480,381 A | 1/1996 | Weston | |
| 5,492,534 A | 2/1996 | Athayde et al. | |
| 5,498,421 A | 3/1996 | Grinstaff et al. | |
| 5,503,538 A | 4/1996 | Wiernicki et al. | |
| 5,514,103 A | 5/1996 | Srisathapat et al. | |
| 5,526,675 A | 6/1996 | Ratton | |
| 5,527,288 A | 6/1996 | Gross et al. | |
| 5,527,307 A | 6/1996 | Srisathapat et al. | |
| 5,551,391 A | 9/1996 | Beck et al. | |
| 5,566,865 A | 10/1996 | Jouillat et al. | |
| 5,569,186 A | 10/1996 | Lord et al. | |
| 5,575,770 A | 11/1996 | Melsky et al. | |
| 5,584,815 A | 12/1996 | Pawelka et al. | |
| 5,616,123 A | 4/1997 | Cheikh | |
| 5,634,779 A | 6/1997 | Eysymontt | |
| 5,639,473 A | 6/1997 | Grinstaff et al. | |
| 5,693,018 A | 12/1997 | Kriesel et al. | |
| 5,704,366 A | 1/1998 | Tacklind et al. | |
| 5,707,212 A | 1/1998 | Matthews | |
| 5,722,367 A | 3/1998 | Izydorek et al. | |
| 5,735,818 A | 4/1998 | Kriesel et al. | |
| 5,746,733 A | 5/1998 | Capaccio et al. | |
| 5,765,729 A | 6/1998 | Miller et al. | |
| 5,848,991 A | 12/1998 | Gross et al. | |
| 5,858,201 A | 1/1999 | Otsuka et al. | |
| 5,863,187 A | 1/1999 | Bensley et al. | |
| 5,876,189 A | 3/1999 | Lukas et al. | |
| 5,880,101 A | 3/1999 | Stankov | |
| 5,885,250 A | 3/1999 | Kriesel et al. | |
| 5,894,992 A | 4/1999 | Liu et al. | |
| 5,902,336 A | 5/1999 | Mishkin | |
| 5,928,201 A | 7/1999 | Poulsen et al. | |
| 5,938,636 A | 8/1999 | Kramer et al. | |
| 5,938,642 A | 8/1999 | Burroughs et al. | |
| 5,948,367 A | 9/1999 | Gmeiner et al. | |
| 5,957,890 A | 9/1999 | Mann et al. | |
| 5,957,895 A | 9/1999 | Sage et al. | |
| 5,960,403 A | 9/1999 | Brown | |
| 5,961,305 A | 10/1999 | Eek et al. | |
| 5,964,377 A | 10/1999 | Demarest et al. | |
| 5,983,728 A * | 11/1999 | Weng | 73/744 |
| 5,988,165 A | 11/1999 | Richey, II et al. | |
| 5,997,501 A | 12/1999 | Gross et al. | |
| 5,997,518 A | 12/1999 | Laibovitz et al. | |
| 6,001,089 A | 12/1999 | Burroughs et al. | |
| 6,003,736 A | 12/1999 | Ljunggren | |
| 6,033,377 A | 3/2000 | Rasmussen et al. | |
| 6,033,393 A | 3/2000 | Balbierz et al. | |
| 6,034,054 A | 3/2000 | Defelippis et al. | |
| 6,037,346 A | 3/2000 | Doherty, Jr. et al. | |
| 6,039,078 A | 3/2000 | Tamari | |
| 6,048,337 A | 4/2000 | Svedman | |
| 6,051,256 A | 4/2000 | Platz et al. | |
| 6,065,289 A | 5/2000 | Phillips | |
| 6,070,761 A | 6/2000 | Bloom et al. | |
| 6,074,374 A | 6/2000 | Fulton | |
| 6,080,130 A | 6/2000 | Castellano | |
| 6,086,562 A | 7/2000 | Jacobsen et al. | |
| 6,102,127 A | 8/2000 | Pierce | |
| 6,110,148 A | 8/2000 | Brown et al. | |
| 6,110,149 A | 8/2000 | Klitgaard et al. | |
| 6,126,642 A | 10/2000 | Kriesel et al. | |
| 6,127,363 A | 10/2000 | Doherty, Jr. et al. | |
| 6,146,361 A | 11/2000 | Dibiasi et al. | |
| 6,156,753 A | 12/2000 | Doherty, Jr. et al. | |
| 6,164,924 A | 12/2000 | Gruett et al. | |
| 6,179,583 B1 | 1/2001 | Weston | |
| 6,212,948 B1 | 4/2001 | Ekdahl et al. | |
| 6,213,120 B1 | 4/2001 | Block et al. | |
| 6,221,378 B1 | 4/2001 | Modi | |
| 6,277,097 B1 | 8/2001 | Mikkelsen et al. | |
| 6,293,756 B1 | 9/2001 | Andersson | |
| 6,302,107 B1 | 10/2001 | Richey, II et al. | |
| 6,306,420 B1 | 10/2001 | Cheikh | |
| 6,340,357 B1 | 1/2002 | Poulsen et al. | |
| 6,342,484 B1 | 1/2002 | Kulkarni et al. | |
| 6,364,865 B1 | 4/2002 | Lavi et al. | |
| 6,413,238 B1 | 7/2002 | Maget | |
| 6,415,961 B2 | 7/2002 | Bonningue | |
| 6,423,035 B1 | 7/2002 | Das et al. | |
| 6,423,344 B1 | 7/2002 | Platz et al. | |
| 6,425,740 B1 | 7/2002 | Jacobsen et al. | |
| 6,433,040 B1 | 8/2002 | Dellamary et al. | |
| 6,436,078 B1 | 8/2002 | Svedman | |
| 6,446,513 B1 | 9/2002 | Henderson | |
| 6,474,219 B2 | 11/2002 | Klitmose et al. | |
| 6,478,771 B1 | 11/2002 | Lavi et al. | |
| 6,482,186 B1 | 11/2002 | Douglas et al. | |

(56) References Cited

U.S. PATENT DOCUMENTS

| | | | |
|---|---|---|---|
| 6,484,906 | B2 | 11/2002 | Bonningue |
| 6,489,346 | B1 | 12/2002 | Phillips |
| 6,508,266 | B2 * | 1/2003 | Iritani et al. ............ 137/312 |
| 6,533,183 | B2 | 3/2003 | Aasmul et al. |
| 6,537,251 | B2 | 3/2003 | Klitmose |
| 6,540,161 | B1 | 4/2003 | Gordon |
| 6,540,996 | B1 | 4/2003 | Zwaal et al. |
| 6,544,229 | B1 | 4/2003 | Danby et al. |
| 6,551,992 | B1 | 4/2003 | Defelippis et al. |
| 6,561,978 | B1 | 5/2003 | Conn et al. |
| 6,565,872 | B2 | 5/2003 | Wu et al. |
| 6,579,496 | B1 | 6/2003 | Fausset et al. |
| 6,582,393 | B2 | 6/2003 | Sage, Jr. |
| 6,582,418 | B1 | 6/2003 | Verbeek et al. |
| 6,592,860 | B1 | 7/2003 | Levy et al. |
| 6,592,904 | B2 | 7/2003 | Platz et al. |
| 6,602,241 | B2 | 8/2003 | Makower et al. |
| 6,612,535 | B1 | 9/2003 | Tai et al. |
| 6,613,019 | B2 | 9/2003 | Munk |
| 6,620,379 | B1 | 9/2003 | Piuk et al. |
| 6,629,934 | B2 | 10/2003 | Mault et al. |
| 6,641,562 | B1 | 11/2003 | Peterson |
| 6,641,565 | B1 | 11/2003 | Lavi et al. |
| 6,641,566 | B2 | 11/2003 | Douglas et al. |
| 6,645,181 | B1 | 11/2003 | Lavi et al. |
| 6,656,148 | B2 | 12/2003 | Das et al. |
| 6,656,158 | B2 | 12/2003 | Mahoney et al. |
| 6,656,159 | B2 | 12/2003 | Flaherty |
| 6,663,602 | B2 | 12/2003 | Møller |
| 6,669,669 | B2 | 12/2003 | Flaherty et al. |
| 6,679,865 | B2 | 1/2004 | Shekalim |
| 6,689,108 | B2 | 2/2004 | Lavi et al. |
| 6,692,457 | B2 | 2/2004 | Flaherty |
| 6,699,218 | B2 | 3/2004 | Flaherty et al. |
| 6,699,885 | B2 | 3/2004 | Phillips |
| 6,702,779 | B2 | 3/2004 | Connelly et al. |
| 6,705,845 | B2 | 3/2004 | Krieger et al. |
| 6,706,689 | B2 | 3/2004 | Coolidge et al. |
| 6,715,516 | B2 | 4/2004 | Ohms et al. |
| 6,723,068 | B2 | 4/2004 | Lavi et al. |
| 6,723,072 | B2 | 4/2004 | Flaherty et al. |
| 6,740,059 | B2 | 5/2004 | Flaherty |
| 6,743,202 | B2 | 6/2004 | Hirschman et al. |
| 6,749,587 | B2 | 6/2004 | Flaherty |
| 6,755,810 | B1 | 6/2004 | Buch Rasmussen et al. |
| 6,786,246 | B2 | 9/2004 | Ohms et al. |
| 6,805,122 | B2 | 10/2004 | Richey, II et al. |
| 6,811,792 | B2 | 11/2004 | Roser et al. |
| 6,814,547 | B2 | 11/2004 | Childers et al. |
| 6,827,898 | B1 | 12/2004 | Fausset et al. |
| 6,830,558 | B2 | 12/2004 | Flaherty et al. |
| 6,847,898 | B1 | 1/2005 | Chen et al. |
| 6,854,620 | B2 | 2/2005 | Ramey |
| 6,880,564 | B2 | 4/2005 | Erickson |
| 6,886,556 | B2 | 5/2005 | Fuchs |
| 6,893,415 | B2 | 5/2005 | Madsen et al. |
| 6,906,028 | B2 | 6/2005 | Defelippis et al. |
| 6,908,591 | B2 | 6/2005 | Macphee et al. |
| 6,913,933 | B2 | 7/2005 | Jacobs et al. |
| 6,916,159 | B2 | 7/2005 | Rush et al. |
| 6,923,180 | B2 | 8/2005 | Richey, II et al. |
| 6,930,093 | B2 | 8/2005 | Brantl |
| 6,931,845 | B2 | 8/2005 | Schaeffer |
| 6,932,796 | B2 | 8/2005 | Sage et al. |
| 6,935,539 | B2 | 8/2005 | Krieger et al. |
| 6,936,035 | B2 | 8/2005 | Rake et al. |
| 6,939,323 | B2 | 9/2005 | Angel et al. |
| 6,946,117 | B1 | 9/2005 | Schutt et al. |
| 6,948,918 | B2 | 9/2005 | Hansen |
| 6,953,323 | B2 | 10/2005 | Childers et al. |
| 6,957,655 | B2 | 10/2005 | Erickson et al. |
| 6,960,192 | B1 | 11/2005 | Flaherty et al. |
| 6,962,151 | B1 | 11/2005 | Knoch et al. |
| 6,966,325 | B2 | 11/2005 | Erickson |
| 6,974,055 | B2 | 12/2005 | Moore et al. |
| 6,974,588 | B1 | 12/2005 | Miranda et al. |
| 6,981,499 | B2 | 1/2006 | Anderson et al. |
| 6,993,795 | B2 | 2/2006 | Prineppi |
| 6,994,691 | B2 | 2/2006 | Ejlersen |
| 6,997,911 | B2 | 2/2006 | Klitmose |
| 6,998,387 | B1 | 2/2006 | Goke et al. |
| 7,008,399 | B2 | 3/2006 | Larsen et al. |
| 7,008,403 | B1 | 3/2006 | Mallett |
| 7,018,336 | B2 | 3/2006 | Enegren et al. |
| 7,018,360 | B2 | 3/2006 | Flaherty et al. |
| 7,029,455 | B2 | 4/2006 | Flaherty |
| 7,033,539 | B2 | 4/2006 | Krensky et al. |
| 7,056,887 | B2 | 6/2006 | Coolidge et al. |
| 7,060,856 | B2 | 6/2006 | Macikenas et al. |
| 7,077,822 | B1 | 7/2006 | Howard, III |
| 7,108,679 | B2 | 9/2006 | Alchas |
| 7,118,351 | B2 | 10/2006 | Effenhauser et al. |
| 7,118,676 | B2 | 10/2006 | Mueth et al. |
| 7,128,727 | B2 | 10/2006 | Flaherty et al. |
| 7,137,964 | B2 | 11/2006 | Flaherty |
| 7,138,141 | B2 | 11/2006 | Platz et al. |
| 7,144,384 | B2 | 12/2006 | Gorman et al. |
| 7,147,839 | B2 | 12/2006 | Sampath et al. |
| 7,150,741 | B2 | 12/2006 | Erickson et al. |
| 7,153,286 | B2 | 12/2006 | Busby et al. |
| 7,189,352 | B2 | 3/2007 | Carpenter et al. |
| 7,195,616 | B2 | 3/2007 | Diller et al. |
| 7,198,751 | B2 | 4/2007 | Carpenter et al. |
| 7,204,958 | B2 | 4/2007 | Olsen et al. |
| 7,225,807 | B2 | 6/2007 | Papania et al. |
| 7,229,288 | B2 | 6/2007 | Stuart et al. |
| 7,237,694 | B2 | 7/2007 | Freudinger |
| 7,255,690 | B2 | 8/2007 | Gray et al. |
| 7,258,864 | B2 | 8/2007 | Clark |
| 7,264,730 | B2 | 9/2007 | Connell et al. |
| 7,268,859 | B2 | 9/2007 | Sage, Jr. et al. |
| 7,288,760 | B2 | 10/2007 | Weitz |
| 7,291,132 | B2 | 11/2007 | Deruntz et al. |
| 7,291,133 | B1 | 11/2007 | Kindler et al. |
| 7,303,549 | B2 | 12/2007 | Flaherty et al. |
| 7,303,680 | B2 | 12/2007 | Connell et al. |
| 7,318,892 | B2 | 1/2008 | Connell et al. |
| 7,341,581 | B2 | 3/2008 | Mallett |
| 7,347,201 | B2 | 3/2008 | Djupesland |
| 7,351,340 | B2 | 4/2008 | Connell et al. |
| 7,357,794 | B2 | 4/2008 | Makower et al. |
| 7,357,899 | B2 | 4/2008 | Gaillard et al. |
| 7,358,091 | B2 | 4/2008 | Phillips et al. |
| 7,374,556 | B2 | 5/2008 | Mallett |
| 7,399,401 | B2 | 7/2008 | Rush |
| 7,399,772 | B2 | 7/2008 | Phillips |
| 7,407,490 | B2 | 8/2008 | Bendsen et al. |
| 7,410,475 | B2 | 8/2008 | Krensky et al. |
| 7,416,644 | B2 | 8/2008 | Bonde |
| 7,425,204 | B2 | 9/2008 | Angel et al. |
| 7,427,275 | B2 | 9/2008 | Deruntz et al. |
| 7,435,717 | B2 | 10/2008 | Bisgaier et al. |
| 7,467,027 | B2 | 12/2008 | Ding et al. |
| 7,481,218 | B2 | 1/2009 | Djupesland |
| 7,497,841 | B2 | 3/2009 | Alchas |
| 7,500,959 | B2 | 3/2009 | Munk |
| 7,517,440 | B2 | 4/2009 | Anex et al. |
| 7,517,530 | B2 | 4/2009 | Clark |
| 7,524,304 | B2 | 4/2009 | Genosar |
| 7,530,968 | B2 | 5/2009 | Gonnelli |
| 7,543,581 | B2 | 6/2009 | Djupesland |
| 7,548,314 | B2 | 6/2009 | Altobelli et al. |
| 7,553,813 | B2 | 6/2009 | Unemori |
| 7,559,223 | B2 | 7/2009 | Chen et al. |
| 7,588,046 | B1 | 9/2009 | Erickson |
| 7,594,889 | B2 | 9/2009 | St. Ores et al. |
| 7,606,615 | B2 | 10/2009 | Makower et al. |
| 7,642,232 | B2 | 1/2010 | Green et al. |
| 7,678,084 | B2 | 3/2010 | Judson et al. |
| 7,678,762 | B2 | 3/2010 | Green et al. |
| 7,678,763 | B2 | 3/2010 | Green et al. |
| 7,681,570 | B2 | 3/2010 | Vedrine et al. |
| 7,682,563 | B2 | 3/2010 | Carpenter et al. |
| 7,683,029 | B2 | 3/2010 | Hindle et al. |

(56) References Cited

U.S. PATENT DOCUMENTS

| | | |
|---|---|---|
| 7,695,454 B2 | 4/2010 | Barron et al. |
| 7,699,767 B2 | 4/2010 | Mueth et al. |
| 7,704,237 B2 | 4/2010 | Fisher et al. |
| 7,704,238 B2 | 4/2010 | Diller et al. |
| 7,713,240 B2 | 5/2010 | Istoc et al. |
| 7,726,955 B2 | 6/2010 | Ryser et al. |
| 7,727,181 B2 | 6/2010 | Rush |
| 7,740,708 B2 | 6/2010 | Lofton et al. |
| 7,753,873 B2 | 7/2010 | Rush |
| 7,775,975 B2 | 8/2010 | Brister et al. |
| 7,789,849 B2 | 9/2010 | Busby et al. |
| 7,811,279 B2 | 10/2010 | John |
| 7,815,595 B2 | 10/2010 | Busby et al. |
| 7,815,609 B2 | 10/2010 | Hines et al. |
| 7,815,622 B2 | 10/2010 | Istoc et al. |
| 7,837,648 B2 | 11/2010 | Blair et al. |
| 7,857,791 B2 | 12/2010 | Jacobs et al. |
| 7,887,505 B2 | 2/2011 | Flaherty |
| 7,914,500 B2 | 3/2011 | Gafner-Geiser et al. |
| 7,922,458 B2 | 4/2011 | Rush et al. |
| 7,922,899 B2 | 4/2011 | Vasta et al. |
| 7,935,104 B2 | 5/2011 | Yodfat et al. |
| 7,938,802 B2 | 5/2011 | Bicknell et al. |
| 7,942,069 B2 | 5/2011 | Peterson |
| 7,951,114 B2 | 5/2011 | Rush et al. |
| 7,957,984 B1 | 6/2011 | Vallone |
| 7,963,945 B2 | 6/2011 | Miller et al. |
| 7,967,010 B2 | 6/2011 | Vedrine et al. |
| 7,967,810 B2 | 6/2011 | Freedman et al. |
| 7,970,620 B2 | 6/2011 | Brown |
| 7,976,493 B2 | 7/2011 | Carter et al. |
| 7,976,500 B2 | 7/2011 | Adams et al. |
| 7,981,076 B2 | 7/2011 | Sullivan et al. |
| 7,985,057 B2 | 7/2011 | Haar |
| 7,988,850 B2 | 8/2011 | Roncadi et al. |
| 7,993,108 B2 | 8/2011 | Rush et al. |
| 8,002,700 B2 | 8/2011 | Ferek-Petric et al. |
| 8,007,460 B2 | 8/2011 | Gelfand et al. |
| 8,026,215 B2 | 9/2011 | Unemori |
| 8,026,227 B2 | 9/2011 | Hausheer |
| 8,029,245 B2 | 10/2011 | Rush et al. |
| 8,029,250 B2 | 10/2011 | Rush et al. |
| 8,029,454 B2 | 10/2011 | Kelly et al. |
| 8,032,226 B2 | 10/2011 | Miller et al. |
| 8,034,019 B2 | 10/2011 | Nair et al. |
| 8,047,202 B2 | 11/2011 | Djupesland |
| 8,047,811 B2 | 11/2011 | Rush et al. |
| 8,047,812 B2 | 11/2011 | Rush et al. |
| 8,056,582 B2 | 11/2011 | DiPerna |
| 8,062,256 B2 | 11/2011 | Carter et al. |
| 8,062,257 B2 | 11/2011 | Moberg et al. |
| 8,066,629 B2 | 11/2011 | Dlugos |
| 8,066,665 B2 | 11/2011 | Rush et al. |
| 8,066,671 B2 | 11/2011 | Busby et al. |
| 8,067,031 B2 | 11/2011 | Daniloff et al. |
| 8,070,726 B2 | 12/2011 | Gonnelli et al. |
| 8,071,075 B2 | 12/2011 | Reed et al. |
| 8,075,522 B2 | 12/2011 | Larsen et al. |
| 8,075,527 B2 | 12/2011 | Rush et al. |
| 8,075,919 B2 | 12/2011 | Brown et al. |
| 8,079,983 B2 | 12/2011 | Rush et al. |
| 8,079,984 B2 | 12/2011 | Rush et al. |
| 8,083,718 B2 | 12/2011 | Rush et al. |
| 8,090,430 B2 | 1/2012 | Makower et al. |
| 8,105,265 B2 | 1/2012 | Demers et al. |
| 8,105,269 B2 | 1/2012 | Zhou |
| 8,105,280 B2 | 1/2012 | Iddan et al. |
| 8,119,593 B2 | 2/2012 | Richardson et al. |
| 8,128,597 B2 | 3/2012 | Cross et al. |
| 8,152,764 B2 | 4/2012 | Istoc et al. |
| 8,182,462 B2 | 5/2012 | Istoc et al. |
| 8,202,267 B2 | 6/2012 | Field et al. |
| 8,231,572 B2 | 7/2012 | Carter et al. |
| 8,249,894 B2 | 8/2012 | Brown |
| 8,260,630 B2 | 9/2012 | Brown |
| 8,287,495 B2 | 10/2012 | Michaud et al. |
| 8,290,788 B2 | 10/2012 | Brown |
| 8,292,876 B2 | 10/2012 | Kriesel et al. |
| 8,298,183 B2 | 10/2012 | Menot et al. |
| 8,298,184 B2 | 10/2012 | Diperna et al. |
| 8,328,754 B2 | 12/2012 | Estes et al. |
| 8,361,030 B2 | 1/2013 | Carter |
| 8,372,040 B2 | 2/2013 | Huang et al. |
| 8,385,972 B2 | 2/2013 | Bochenko et al. |
| 8,407,063 B2 | 3/2013 | Brown |
| 8,408,421 B2 | 4/2013 | DiPerna |
| 8,448,824 B2 | 5/2013 | DiPerna |
| 8,573,027 B2 * | 11/2013 | Rosinko et al. ............... 73/1.35 |
| 2001/0000282 A1 | 4/2001 | Poleshuk et al. |
| 2002/0018720 A1 | 2/2002 | Carlisle et al. |
| 2002/0040208 A1 | 4/2002 | Flaherty et al. |
| 2002/0072733 A1 | 6/2002 | Flaherty |
| 2002/0117214 A1 | 8/2002 | Tucker et al. |
| 2003/0055380 A1 | 3/2003 | Flaherty |
| 2003/0060765 A1 | 3/2003 | Campbell et al. |
| 2003/0109836 A1 | 6/2003 | Shekalim |
| 2003/0216683 A1 | 11/2003 | Shekalim |
| 2004/0073161 A1 | 4/2004 | Tachibana |
| 2004/0078028 A1 | 4/2004 | Flaherty et al. |
| 2004/0092865 A1 | 5/2004 | Flaherty et al. |
| 2004/0116866 A1 | 6/2004 | Gorman et al. |
| 2004/0204673 A1 | 10/2004 | Flaherty |
| 2004/0260233 A1 | 12/2004 | Garibotto et al. |
| 2005/0137530 A1 | 6/2005 | Campbell et al. |
| 2005/0272989 A1 | 12/2005 | Shah et al. |
| 2006/0041229 A1 | 2/2006 | Garibotto et al. |
| 2006/0076236 A1 | 4/2006 | Shah et al. |
| 2006/0147313 A1 | 7/2006 | Zengerie et al. |
| 2006/0229557 A1 | 10/2006 | Fathallah et al. |
| 2006/0282290 A1 | 12/2006 | Flaherty et al. |
| 2007/0000337 A1 | 1/2007 | Gross |
| 2007/0003434 A1 | 1/2007 | Padmanabhan et al. |
| 2007/0227907 A1 | 10/2007 | Shah et al. |
| 2007/0264130 A1 | 11/2007 | Mallett |
| 2008/0026473 A1 | 1/2008 | Wang et al. |
| 2008/0029173 A1 | 2/2008 | DiPerna |
| 2008/0092969 A1 | 4/2008 | DiPerna |
| 2008/0196762 A1 | 8/2008 | Mallett et al. |
| 2009/0062767 A1 | 3/2009 | Van Antwerp et al. |
| 2009/0088731 A1 | 4/2009 | Campbell et al. |
| 2009/0131863 A1 | 5/2009 | Carlisle et al. |
| 2009/0191067 A1 | 7/2009 | DiPerna |
| 2009/0192724 A1 | 7/2009 | Brauker et al. |
| 2009/0217982 A1 | 9/2009 | DiPerna |
| 2009/0247982 A1 | 10/2009 | Krulevitch et al. |
| 2009/0287180 A1 | 11/2009 | Diperna |
| 2010/0008795 A1 | 1/2010 | Diperna |
| 2010/0030045 A1 | 2/2010 | Gottlieb et al. |
| 2010/0036327 A1 | 2/2010 | DiPerna |
| 2010/0065579 A1 | 3/2010 | Diperna |
| 2010/0081993 A1 | 4/2010 | O'Connor |
| 2010/0087777 A1 | 4/2010 | Hopping et al. |
| 2010/0096019 A1 | 4/2010 | DiPerna |
| 2010/0145303 A1 | 6/2010 | Yodfat et al. |
| 2010/0174230 A1 | 7/2010 | Istoc et al. |
| 2010/0218586 A1 | 9/2010 | Rosinko et al. |
| 2010/0249706 A1 | 9/2010 | Clemente |
| 2010/0262078 A1 | 10/2010 | Blomquist |
| 2010/0262434 A1 | 10/2010 | Shaya |
| 2010/0280329 A1 | 11/2010 | Randløv et al. |
| 2010/0286563 A1 | 11/2010 | Bryer et al. |
| 2011/0009798 A1 | 1/2011 | Kelly et al. |
| 2011/0009846 A1 | 1/2011 | Istoc et al. |
| 2011/0071465 A1 | 3/2011 | Wang et al. |
| 2011/0092894 A1 | 4/2011 | Mcgill et al. |
| 2011/0111794 A1 | 5/2011 | Bochenko et al. |
| 2011/0118700 A1 | 5/2011 | Remde |
| 2011/0120206 A1 | 5/2011 | Troughton et al. |
| 2011/0125085 A1 | 5/2011 | Mcgill et al. |
| 2011/0144569 A1 | 6/2011 | Britton et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |

(56) References Cited

U.S. PATENT DOCUMENTS

| | | |
|---|---|---|
| 2011/0166544 A1 | 7/2011 | Verhoef et al. |
| 2012/0029433 A1 | 2/2012 | Michaud et al. |
| 2012/0029708 A1 | 2/2012 | Miller et al. |
| 2012/0030610 A1 | 2/2012 | Diperna et al. |
| 2013/0053816 A1 | 2/2013 | DiPerna |
| 2013/0306191 A1 | 11/2013 | Metzmaker et al. |
| 2013/0324928 A1 | 12/2013 | Kruse |
| 2014/0276538 A1 | 9/2014 | Michaud |

FOREIGN PATENT DOCUMENTS

| | | |
|---|---|---|
| WO | WO9100753 A1 | 1/1991 |
| WO | WO9819627 A1 | 5/1998 |
| WO | WO0228532 A9 | 5/2003 |
| WO | WO2007065944 A1 | 6/2007 |
| WO | WO2008024812 A3 | 7/2008 |
| WO | WO2007119149 A8 | 8/2008 |
| WO | WO2009016636 A3 | 3/2009 |
| WO | WO2007106232 A3 | 4/2009 |
| WO | WO2009143188 A3 | 4/2010 |
| WO | WO2010099490 A3 | 1/2011 |
| WO | WO2010096449 A3 | 3/2011 |
| WO | WO2011014704 A3 | 6/2011 |
| WO | WO2011017667 A3 | 7/2011 |

OTHER PUBLICATIONS

Application and File History for U.S. Appl. No. 12/393,973, filed Feb. 26, 2009, inventor DiPerna.
Application and File History for U.S. Appl. No. 12/189,064, filed Aug. 8, 2008, inventor DiPerna.
Application and File History for U.S. Appl. No. 11/462,962, filed Aug. 7, 2006, inventor DiPerna.
Application and File History for U.S. Appl. No. 11/694,841, filed Mar. 30, 2007, inventor DiPerna.
Application and File History for U.S. Appl. No. 12/646,881, filed Dec. 23, 2009, inventor DiPerna.
Application and File History for U.S. Appl. No. 12/189,070, filed Aug. 8, 2008, inventor DiPerna.
Application and File History for U.S. Appl. No. 12/039,693, filed Feb. 28, 2008, inventor DiPerna.
Application and File History for U.S. Appl. No. 12/714,299, filed Feb. 26, 2010, inventor Rosinko et al.
International Search Report and Written Opinion for International Application No. PCT/US2003/022703 dated Sep. 10, 2004.
International Search Report for International Application No. PCT/2007/060633 dated Jul. 23, 2007.
International Preliminary Report for International Application No. PCT/2007/060633 dated Jul. 29, 2008 and Written Opinion dated Jul. 23, 2007.
International Search Report and Written Opinion for International Application No. PCT/US2009/035022 mailed May 29, 2009.
International Preliminary Report on Patentability mailed on: Sep. 10, 2010 in International Application: PCT/US2009/035022 and Written Opinion dated May 29, 2009.
International Preliminary Report on Patentability mailed on: Oct. 6, 2009 in International Application: PCT/US2008/058044 and Written Opinion dated Aug. 11, 2008.
Arrow International Europe Web Page for: Multiple Lumen Peripheral Catheter, Product No. IV-01150, printed from the internet on Nov. 15, 2011.
AngioDynamics, Smart Port, Power-Injectable Ports Product Brochure, Copyright 2010 AngioDynamics, Inc.
i-port Advance product brochure, distributed by: Patton Medical Devices and Manufactured by Unomedical, a Cardiovascular Company, Copyright, 2007-2010 Patton Medical Devices, LP.
International Search Report and Written Opinion mailed on: Feb. 17, 2011 in International Application: PCT/US2009/049110.
International Search Report and Written Opinion mailed on: Jan. 27, 2010 in International Application: PCT/US2009/049110.
International Preliminary Report and Written Opinion mailed on: Feb. 17, 2011 in International Application: PCT/2009/049116.
International Search Report and Written Opinion mailed on: Feb. 4, 2010 in International Application: PCT/2009/049116.
International Preliminary Report on Patentability mailed on Aug. 5, 2010 in International Application: PCT/US2009/031906.
International Search Report and Written Opinion mailed on Jul. 28, 2009 in International Application: PCT/US2009/031906.
International Search Report and Written Opinion mailed on: Jan. 4, 2010 in International Application: PCT/US2009/044569.
International Preliminary Report on Patentability mailed: Dec. 2, 2010, in International Patent Application No. PCT/US2009/044569.
International Preliminary Report on Patentability mailed on Mar. 31, 2011 in International Application: PCT/2009/057208.
International Search Report and Written Opinion mailed on Apr. 1, 2010 in International Application: PCT/2009/057208.
International Search Report and Written Opinion mailed on: Sep. 30, 2010 in International Application: PCT/2010/025663.
International Preliminary Report on Patentability mailed on Mar. 31, 2011 in International Application: PCT/2009/57591.
International Search Report and Written Opinion mailed on Apr. 12, 2010 in International Application: PCT/2009/57591.
Miller, John E., "The Reciprocating Pump, Theory, Design and Use," Chapter 1, "Pump Types", Krieger Publishing Company, Malabar, Florida 1995.
Spring Zone Insulin Delivery System Product Brochure, Copyright 2011 Spring (formerly NiliMEDIX), a D-Medical company.
Extended European Search Report mailed on: Mar. 6, 2012 in European Application No. EP 09751416 based on International Application No. PCT/US2009/044569.
International Search Report, Written Opinion for International Application No. PCT/US2010/043789 dated Apr. 11, 2011.
Australian Patent Examination Report No. 1 for Australian App. No. 2010217760 dated Mar. 13, 2014.
Australian Notice of Acceptance for Australian App No. 2010217760 dated Mar. 31, 2015.

\* cited by examiner

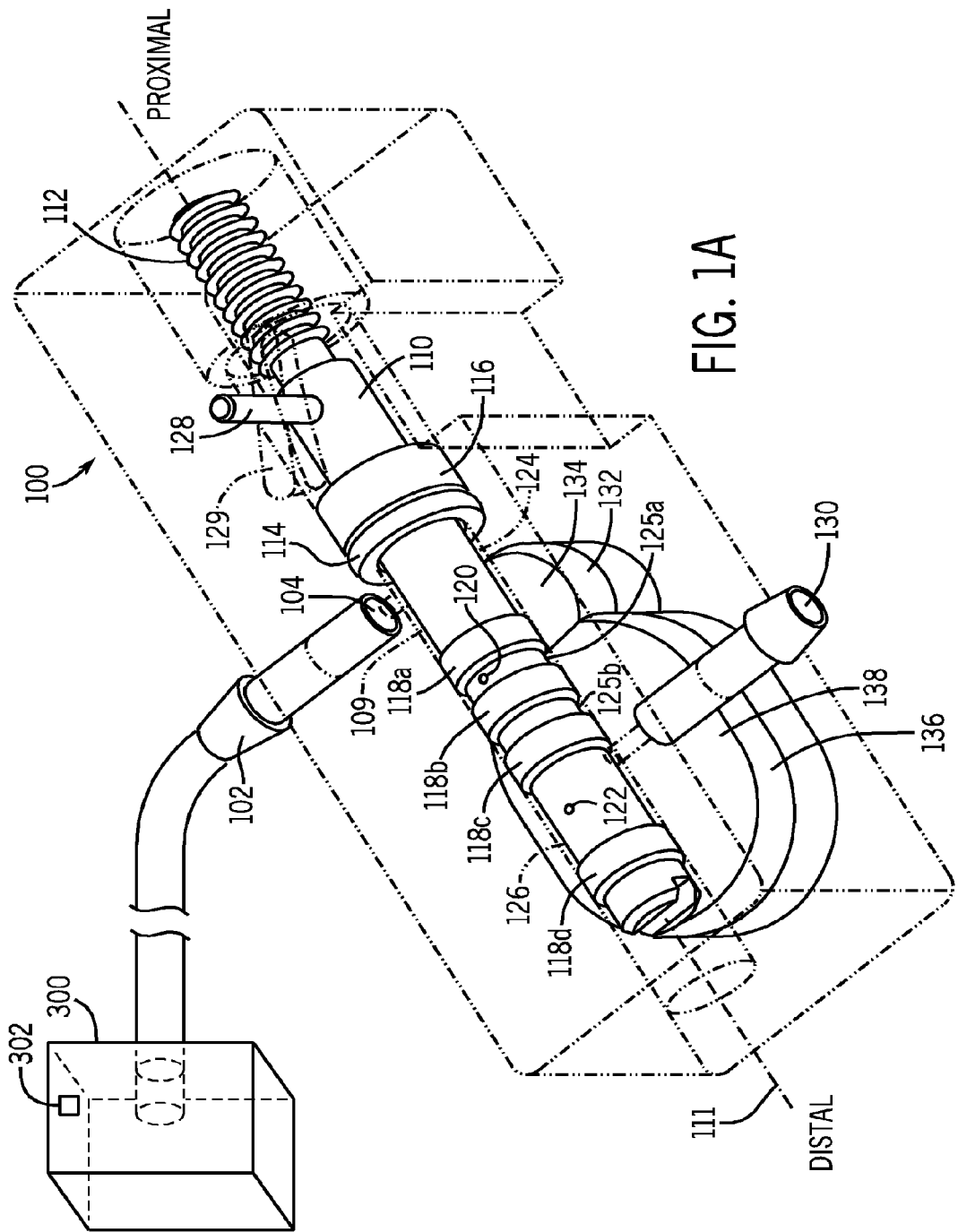

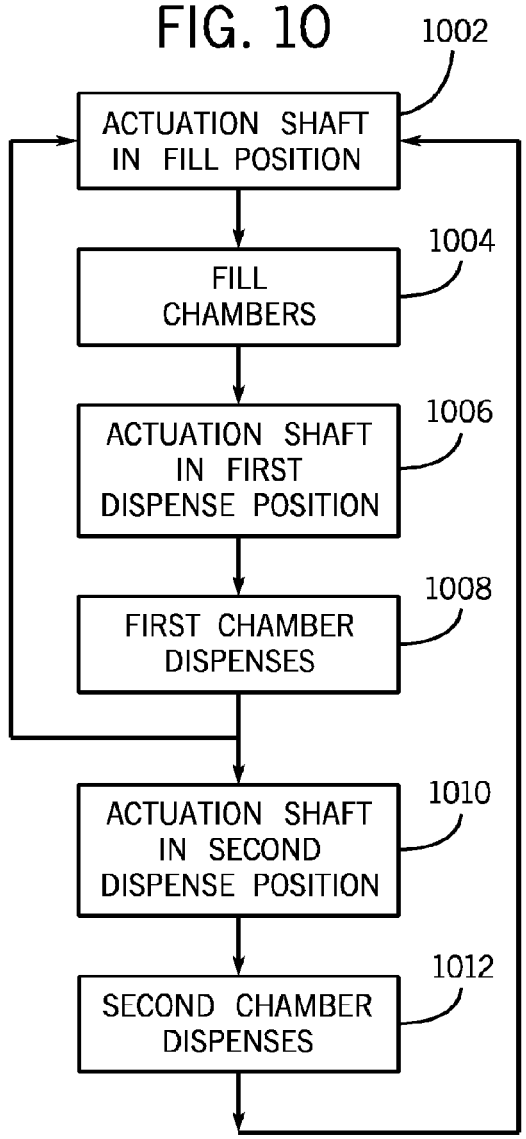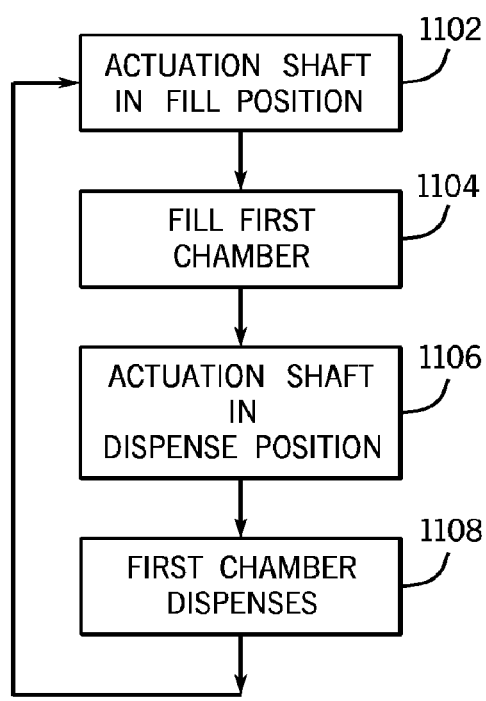

US 9,250,106 B2

METHODS AND DEVICES FOR DETERMINATION OF FLOW RESERVOIR VOLUME

RELATED APPLICATION

This application is a continuation of application Ser. No. 12/714,299 filed Feb. 26, 2010, which claims the benefit of U.S. Provisional Application No. 61/156,405, filed Feb. 27, 2009 and U.S. Provisional Patent Application Ser. No. 61/184,282, filed Jun. 4, 2009, each of which is hereby fully incorporated herein by reference.

BACKGROUND

This disclosure relates to methods and devices for the determination of flow reservoir volumes.

SUMMARY

A novel enhanced flow metering device is adapted for disposing into a flow material reservoir a known volume of flow material whereby software used in conjunction with a pressure sensor may be calibrated. Additionally, by knowing or determining the volume of a proximal flow space provides novel methods for determining the volume of flow material delivered, and with accuracy. Moreover, it provides for a novel safety device, whereby determination of the correct functioning of sensors measuring the volume reservoirs.

DRAWINGS

The above-mentioned features and objects of the present disclosure will become more apparent with reference to the following description taken in conjunction with the accompanying drawings wherein like reference numerals denote like elements and in which:

FIG. 1A is a perspective view of an embodiment of the flow metering device of the present disclosure having two chambers actuated by a threaded device;

FIG. 10 is a flow diagram of embodiments of a method for dispensing a flow material through the stopcock devices of the present disclosure;

FIG. 11 is a flow diagram of embodiments of a method for dispensing a flow material through the stopcock devices of the present disclosure;

DETAILED DESCRIPTION

Figure 1B:
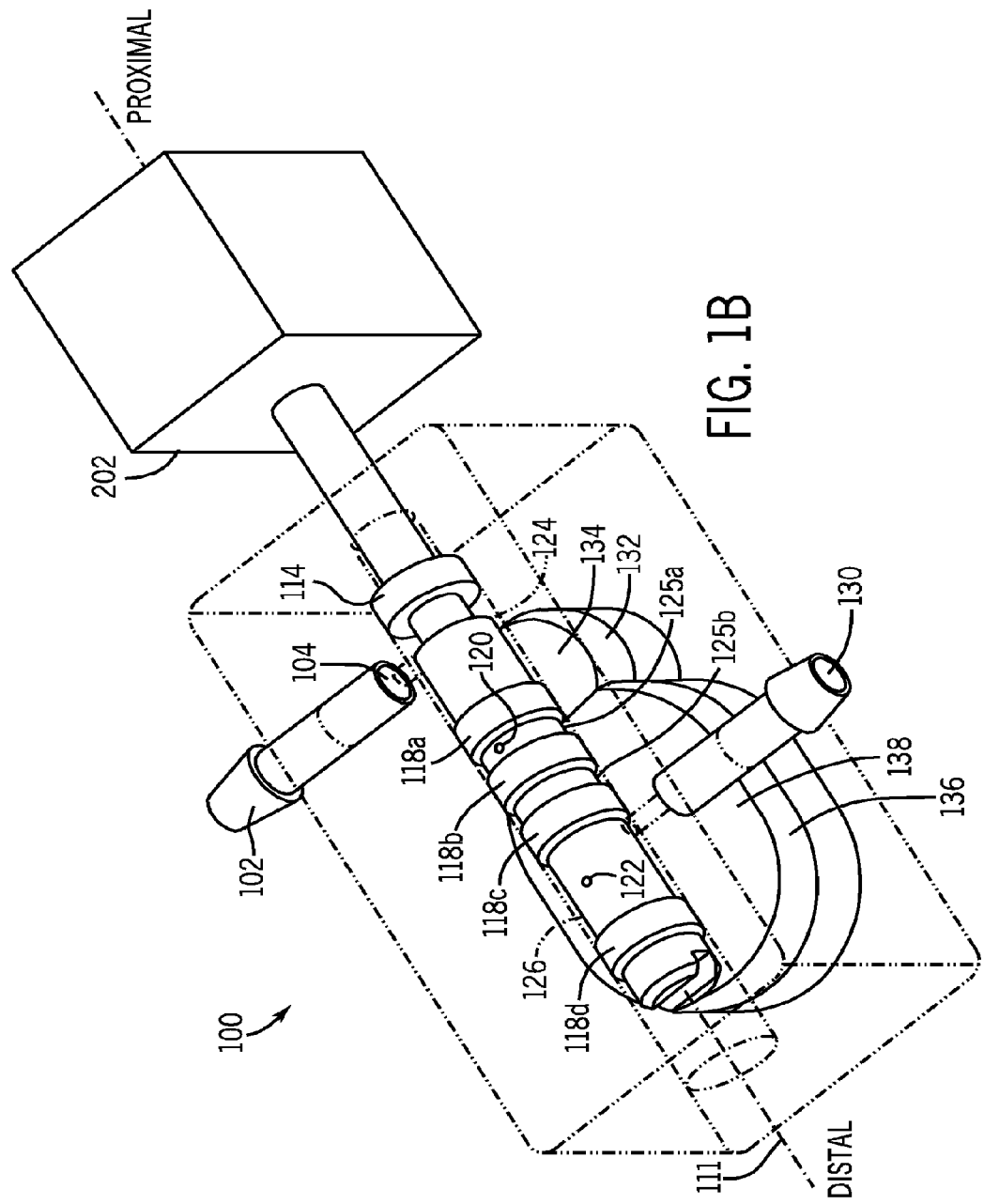
FIG. 1B is a perspective view of an embodiment of the flow metering device of the present disclosure having two chambers actuated by a wire.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

As used herein, the term "real time" shall be understood to mean the instantaneous moment of an event or condition, or the instantaneous moment of an event or condition plus a short period of elapsed time used to make relevant measurements, computations, etc., and to communicate such measurement, computation, etc., wherein the state of an event or condition being measured is substantially the same as that of the instantaneous moment irrespective of the elapsed time interval. Used in this context "substantially the same" shall be understood to mean that the data for the event or condition remains useful for the purpose for which it is being gathered after the elapsed time period.

As used herein, the term "fluid" shall mean a gas or a liquid.

As used herein, the term "flow material" shall mean a fluid that is intended for delivery to a target.

As used herein, the term "fill" and "filling" shall mean increasing the amount of a fluid in a chamber by some percentage of the total volume of the chamber up to 100%.

Disclosed herein are methods and devices for determining the volume of flow material reservoirs and for calibrating sensors used to measure volumes in pumps, such as infusion pumps. The methods use flow metering devices disclosed herein to deliver a known volume of flow material back into a flow material reservoir in each metering cycle. Additionally, the present disclosure provides a method for detecting integrity or failure of the mechanical components of the pumps and the flow metering device.

Calculation of volume and overall flow rate of a pump are disclosed in U.S. Pat. Nos. 7,008,403; 7,341,581; and 7,374,556; U.S. Utility Patent Application Pub. Nos. 2007/0264130; and 2009/0191067 (the contents of each above listed patent or patent publication are incorporated herein by reference in their entirety) may be used as devices having flow material reservoirs and as the source of the flow material. These devices typically have sensors disposed therein to measure the volume of the flow material reservoir or to measure the volume of flow material dispersed from the pumps. Other pumps that have both a flow material reservoir and are able to measure the volume of the flow material reservoir or the flow material in the reservoir are expressly contemplated under this disclosure.

Methods for delivery of and determination of the volume of a fluid or flow material are expressly contemplated in this disclosure. Sensors, such as pressure transducers, may be used in connection with the apparatus and methods described herein. Acoustic sensors, including a loud speaker and one or more microphones, may be used to accurately determine the volume of flow material reservoirs, thereby allowing for direct or indirect calculation of the volume of flow material dispensed. Acoustic volume determination technology is disclosed in, e.g., U.S. Pat. Nos. 5,575,310 and 5,755,683 and U.S. Provisional Application Ser. No. 60/789,243, each of which is incorporated herein by reference in its entirety. U.S. Pat Application Publication No. 2007/0219496, which is incorporated herein by reference in its entirety, discloses still further methods for the determination of the volume of flow material reservoirs, including via optical, capacitive, deflection measurement methods (detecting deflection of a membrane as pressure changes), thermal time of flight methods, or other methods for measuring the volume of a chamber.

According to the embodiment illustrated in FIG. 1A, flow metering device 100 is shown. Flow metering device 100 comprises cavity 109 in which actuation shaft 110 is disposed. Actuation shaft 110 has a proximal end terminating with actuation device 112 and a distal end. Actuation shaft 110 further comprises optional actuation guide 128 and at least one fixed seal 118a-118d. According to some embodiments, actuation shaft also comprises at least one shaft channel 121 (see FIG. 5) being defined at the ends by at least one proximal shaft opening 120 and at least one distal shaft opening 122. Flow metering device 100 also comprises at least first chamber 136 having first compressible member 138. According to embodiments The flow metering device 100 illustrated in FIG. 1A also comprises additional chambers, for example second chamber 132 having second compressible member 134.

Figure 1C:
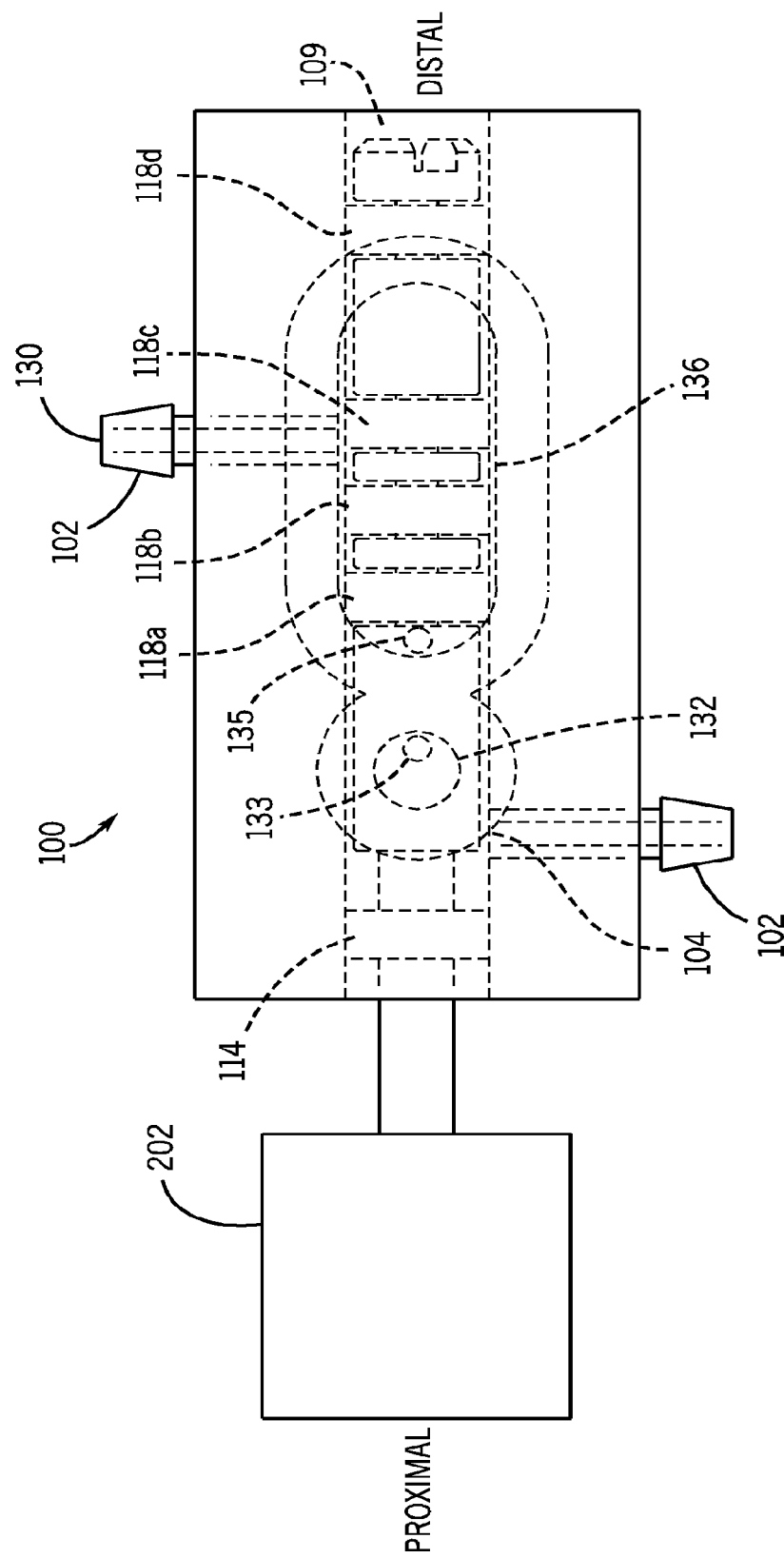
FIG. 1C is a partial plan view of an embodiment of the flow metering device of FIG. 1B.

FIG. 1A-1C illustrate in perspective view a two-chamber version of flow metering device 100, whereby two chambers of varying size are filled with a flow material and one or both chambers 136, 132 are used to dispense flow material to a target. According to the detail shown in FIGS. 1A-1C, flow metering device 100 houses first chamber 136, second chamber 132, and actuation shaft 110.

In use, at least one of first chamber 136 and second chamber 132 is filled with flow material or other fluid through input conduit 104. Input conduit 104 is a conduit through input device 102 terminating at proximal flow space 124 and used for moving flow materials from a flow material source to into flow metering device 100. Input device 102 may be a connector or valve designed to be connected with tubing, conduit, piping, or other devices used to transport flow materials or other fluids.

Flow material is dispensed from flow metering device 100 through output conduit 130. Output conduit 130 is a conduit that allows flow material to move from first chamber 136 or second chamber 132 to a target. Output conduit 130, according to embodiments, may terminate in a connector, for example a luer connector or other industry standard connector, that connects to devices for delivery to the target. For example, if flow metering device 100 is delivering a pharmaceutical, the connector might be a luer device connected to a length of tubing ending in a hypodermic needle for injection of the pharmaceutical. According to embodiments, input conduit 104 and output conduit 130 are not in fluid communication. As illustrated, for example in FIG. 5, output conduit 130 comprises a conduit that transports from material from chamber 136, 132 via output flow space 125a, proximal shaft opening 120, shaft channel 121, distal shaft opening 122, and distal flow space 126. Generally, output conduit is a conduit that is in fluid communication with one or more chambers of flow metering device 100 when actuation shaft 110 is in a dispense position.

Actuation shaft 110 controls the filling and dispensing of first chamber 136 and second chamber 132, depending of the position of actuation shaft 110. Actuation shaft 110 may be disposed in flow metering device cavity 109. As illustrated in FIG. 1A, actuation shaft 110 may be moved with actuation device 112. Actuation device 112 may articulate via actuator 202 (see, e.g., FIGS. 1B, 1C) that effects movement of actuation shaft 110. For example, actuation device 112 comprises a lead screw that is coupled with an actuator 202, for example a motor having opposite threading and able to drive a lead screw. According to embodiments, actuator 202 is a motor, finger, spring, or other implement capable of effecting movement of actuation shaft 110 in cavity 109. In some cases, actuator 202 operates in conjunction with an actuation device 112. In other cases, actuator 202 operates by articulating directly with actuation shaft 110.

In the example of FIG. 1A, actuation device 112 is a series of screw-like threads that articulate with mated screw threads in a motor. Depending on the direction the motor rotates the mated screw threads, actuation shaft 110 moves towards the distal end or towards the proximal end of flow metering device 100.

Actuation device 112 may comprise a nickel-titanium (nitinol) or other shape memory or non-shape memory alloy, metal, plastic material, composite, etc. Actuation device 112 may be a component such as a rigid or semi-rigid wire, rod, or shaft connected to actuator 202, as shown in FIG. 1B. According to these embodiments, actuation device 112 in operation is pushed or pulled to effect movement of actuation shaft 110. According to embodiments where a nitinol actuation device such as, for example, a wire, is used, a spring may be disposed to return the wire to its original position after it is actuated, or a second wire may be disposed to effect the same result. According to similar embodiments, a nitinol actuation device 112 may be returned to a native position through the use of the "self-return" properties of nitinol, e.g., temperature or strain-induced phase transition. Actuation device 112, irrespective of the mechanical design or material used, effects movement of actuation shaft 110 both proximally and distally through flow metering device cavity 109, as desired.

Actuation shaft 110 may be configured to translate along long axis 111 in cavity 109 and may also be configured to rotate around long axis 111. For example and as illustrated in FIG. 1A, actuation guide 128 is disposed in actuation rotation channel 129. As actuation shaft 110 moves in a proximal or distal direction, actuation guide 128 is forced by the walls of actuation rotation channel 129 to rotate actuation shaft 110 around long axis 111 of actuation shaft 110. Rotating actuation shaft 110 helps actuation shaft 110 move proximally and distally through cavity 109 with less friction.

Fixed seals 118a-118d prevent leakage of flow material around them. Fixed seals 118a-118d are disposed around actuation shaft 110 and move with actuation shaft 110.

Articulation of fixed seals 118a-118d with actuation shaft 110 and the walls of flow metering device cavity 109 forms sealed spaces. Flow material in these sealed spaces are trapped therein; accordingly, as actuation shaft 110 moves, so does any fluid trapped in the sealed spaces. Fixed seals may be o-rings, quad-rings, or other devices that form sealed barriers to the flow of fluids, including flow material. Fixed seals 118a-118d (shown in various configuration throughout the figures) are disposed along the length of actuation shaft 110 in various numbers and configurations.

Figure 5:
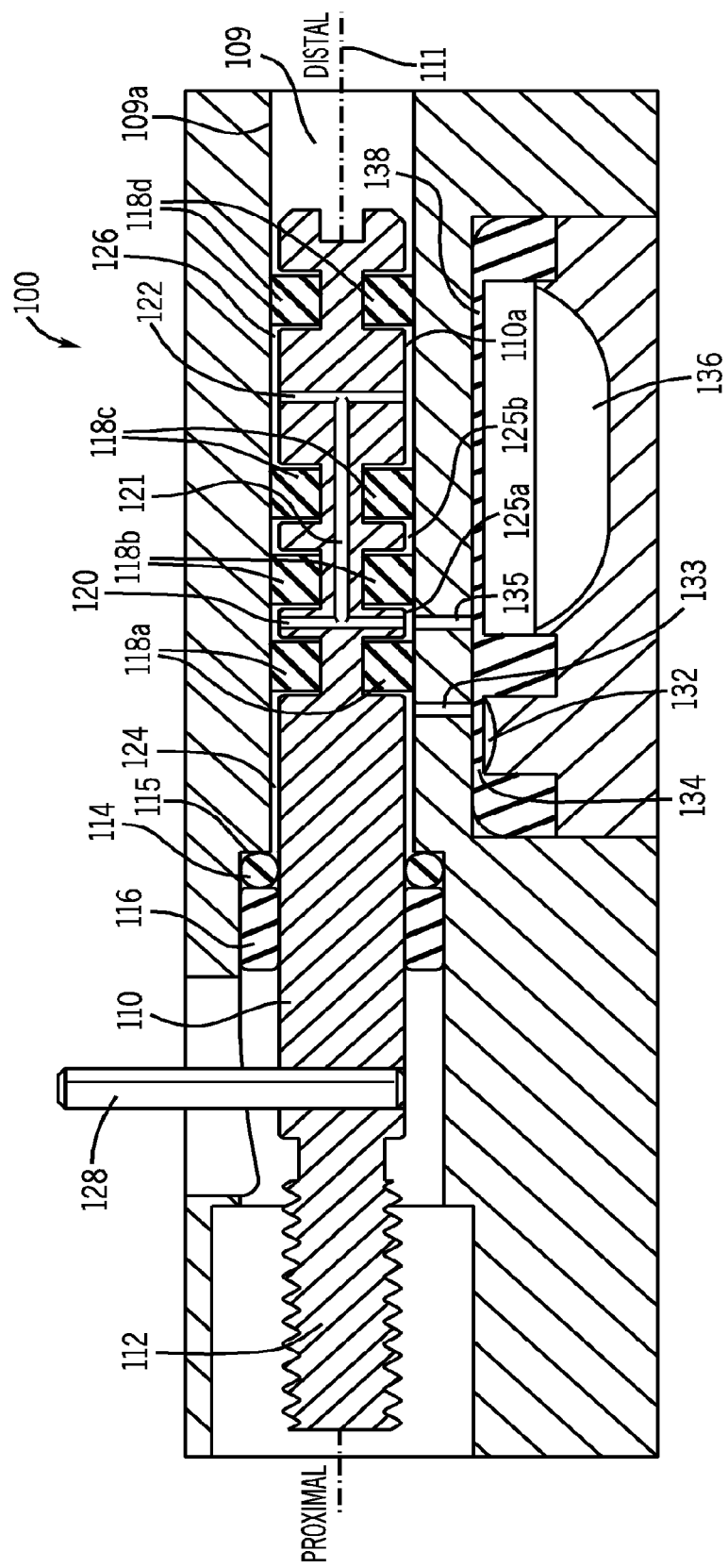
FIG. 5 is a cross-sectional side view of an embodiment of the flow metering device of the present disclosure having two chambers.

In some embodiments, an additional seal, actuation shaft seal 114, is disposed towards the proximal end of actuation shaft 110. Actuation shaft seal 114 is fixed relative to cavity 109 and does not move together with actuation shaft 110. In operation it is held in place by seal retainer 116. As illustrated in FIG. 5, actuation shaft seal 114 may be disposed within flow metering device cavity 109 between seal retainer 116 and flange 115.

As shown, e.g., in FIGS. 1A, 1B, and 5, fixed seals 118a-118d and actuation shaft seal 114 may form a plurality of flow spaces: proximal flow space 124, output flow space 125a, sealed flow space 125b, and distal flow space 126. Each flow space is sealably defined by walls 109a of flow metering device cavity 109, fixed seals 118a-118d (or in the case of proximal flow space 124 by fixed seal 118a and actuation shaft seal 114), and by outer surface 110a of actuation shaft 110. Each space is configured to accommodate the flow of flow material or other fluid.

Devices that have greater than one chamber utilize the multiple fixed seals 118a-118d selectively to allow flow to and from desired chambers. For example, as shown in FIG. 5, shaft channel 121 forms a conduit or channel within actuation shaft 110, allowing flow of fluid such as flow material therethrough. Shaft channel 121 terminates at proximal shaft opening 120 and distal shaft opening 122. In other embodiments, multiple shaft channels 121 may be present. There may exist multiple distal shaft openings 122 (i.e., two or more openings in fluid communication with shaft channel 121 at about the same position along actuation shaft 110), as well as multiple proximal shaft openings 120 to allow for an increased fluid flow rate through shaft channel 121.

As illustrated, shaft channel 121 may be used to bypass one or more fixed seals 118, thereby defining fluid flow paths. As shown in the example of FIG. 5, shaft channel 121 bypasses fixed seals 118b-118c and thereby effects flow from one flow space to another flow space. In particular, shaft channel 121 communicates with output flow space 125a (via proximal shaft opening 120) and distal flow space 126 (via distal shaft opening 122), bypassing sealed flow space 125b. Thus, sealed flow space 125b may be positioned over the conduits leading into the chambers to prevent flow in or out of the chamber over which sealed flow space 125b is positioned, as described in more detail below.

Depending on where shaft channel 121 opens on the proximal end along actuation shaft 110, various flow paths are defined. For example, in the particular configuration with the relative positions of the components shown in FIG. 5, proximal shaft opening 120 puts shaft channel 121 into fluid communication with output flow space 125a and bypass sealed flow space 125b due to the presence of fixed seal 118b. Thus, the contents of first chamber 136 (fluid or flow material) may be dispensed via first chamber conduit 135. Axial movement of actuation shaft 110 within cavity 109 to put shaft channel 121 into fluid communication with second chamber conduit 133 via output flow space 125a will allow any contents of second chamber 132 to be dispensed via second chamber conduit 133. As illustrated in FIG. 5, the contents of first chamber 136 must be dispensed prior to dispensing the contents of second chamber 132.

According to embodiments having more than one chamber, first chamber 136 and second chamber 132 (collectively chambers 132, 136), are disposed to be in fluid communication with the flow spaces via first chamber conduit 135 and second chamber conduit 133, respectively.

Associated with each chamber are compressible members: first compressible member 138 (associated with first chamber 136) and second compressible member 134 (associated with second chamber 132). Compressible members may comprise an elastomeric membrane disposed over each chamber 136, 132. As shown in FIG. 5, for example, first compressible member 138 is an elastomeric membrane that covers first chamber 136; second compressible member 134 is an elastomeric membrane that covers second chamber 132. As fluid or flow material enters each chamber 136, 132 through chamber conduits, for example first chamber conduit 135 or second chamber conduit 133 (respectively), the flow material contacts first compressible member 138 or second compressible member 134, respectively, causing each compressible member 138, 134 to distend into first chamber 136 or second chamber 132, respectively.

Compressible members 138, 134 may comprise other devices and materials as well. According to some embodiments, one or both of the compressible members comprise closed-cell foam. According to other embodiments, one or both of the compressible member comprises other elastomeric materials. According to still other embodiments, one or both compressible members 138, 134 comprise pockets of air contained within a compressible bag or "pillow," or separated by a mechanical device such as a piston or movable barrier. According to still other embodiments, one or both compressible members 138, 134 comprise pneumatic chambers that are controlled via movement of air or vented outside of flow metering device 100.

As illustrated in FIG. 5, first chamber 136 has a larger volume than second chamber 132. Chambers 136 and 132 may have identical volumes or first chamber 132 may have a larger volume than first chamber 136 and be within the scope of the present disclosure. Having variable size chambers such as that shown in FIG. 5, for example, allows for variable aliquot sizes of flow material to be delivered to a target and adds a degree of fine tuning with respect to the overall flow rate of the flow material delivered to a target, for example, in dosing patients with a pharmaceutical. For example, as shown in FIG. 1A, chamber 136, 132 are of different volumes. If insulin is being delivered as the flow material, the dosage may be carefully controlled over time depending on whether an aliquot of insulin from larger chamber 136 or an aliquot of insulin from smaller chamber 132 is delivered. Accordingly, multiple consecutive aliquots may be delivered from smaller chamber 132 to give a diabetic patient basal doses of insulin. However, when a bolus is needed, an aliquot may be delivered from the larger chamber 136.

Figure 2:
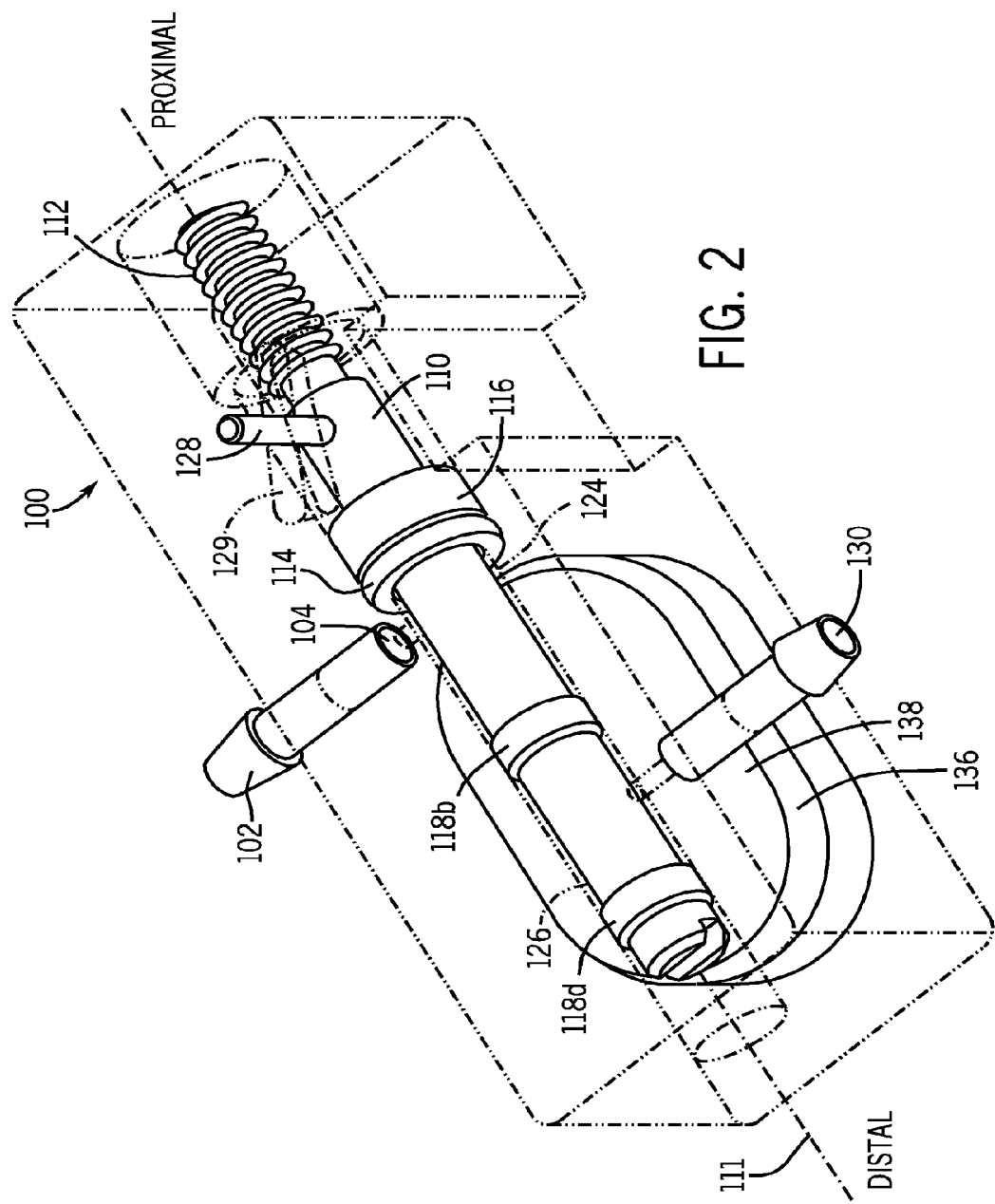
FIG. 2 is a perspective view of an embodiment of the flow metering device of the present disclosure having one chamber.
Figure 3:
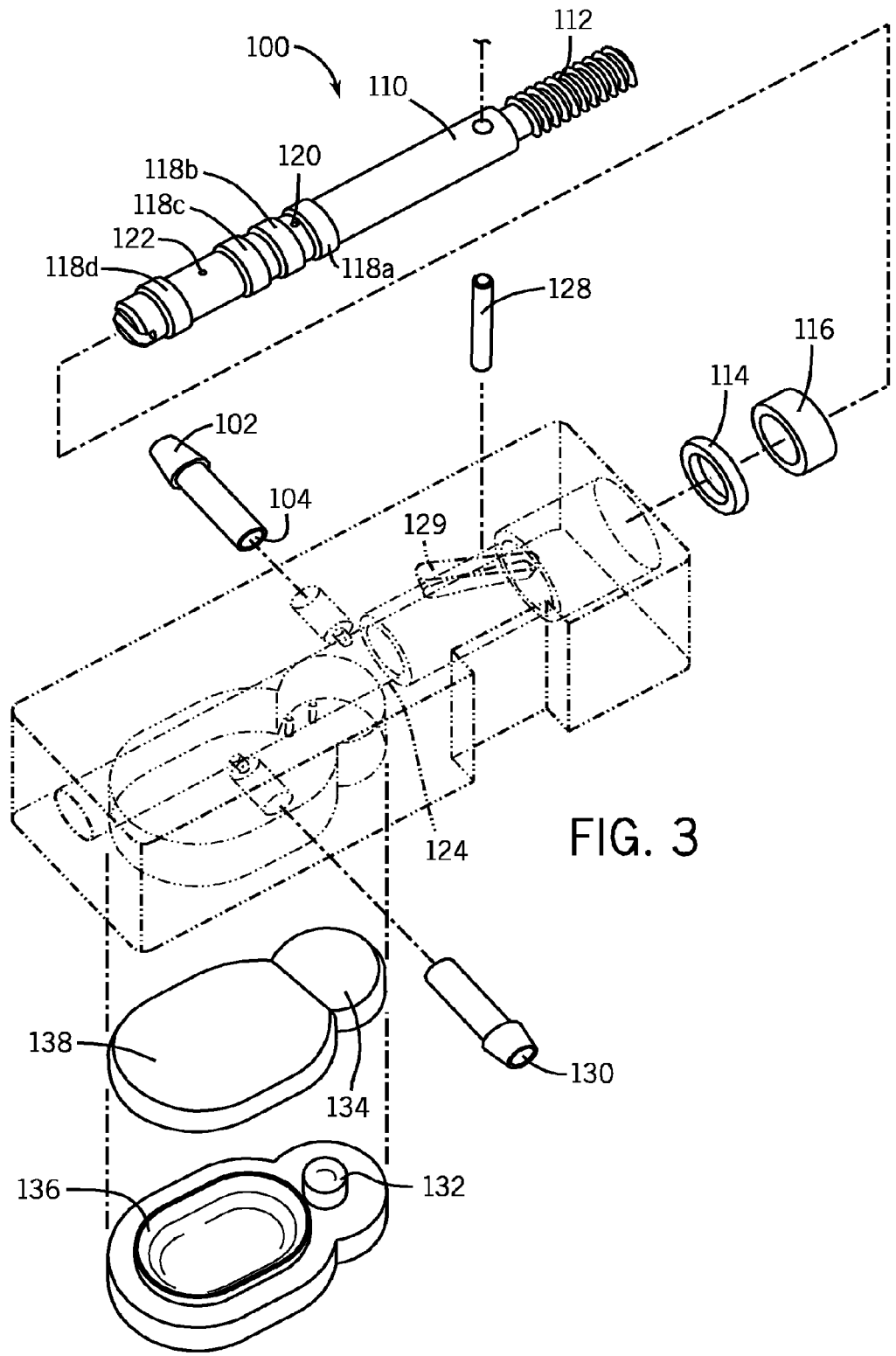
FIG. 3 is an exploded view of an embodiment of the flow metering device of the present disclosure having two chambers.
Figure 4:
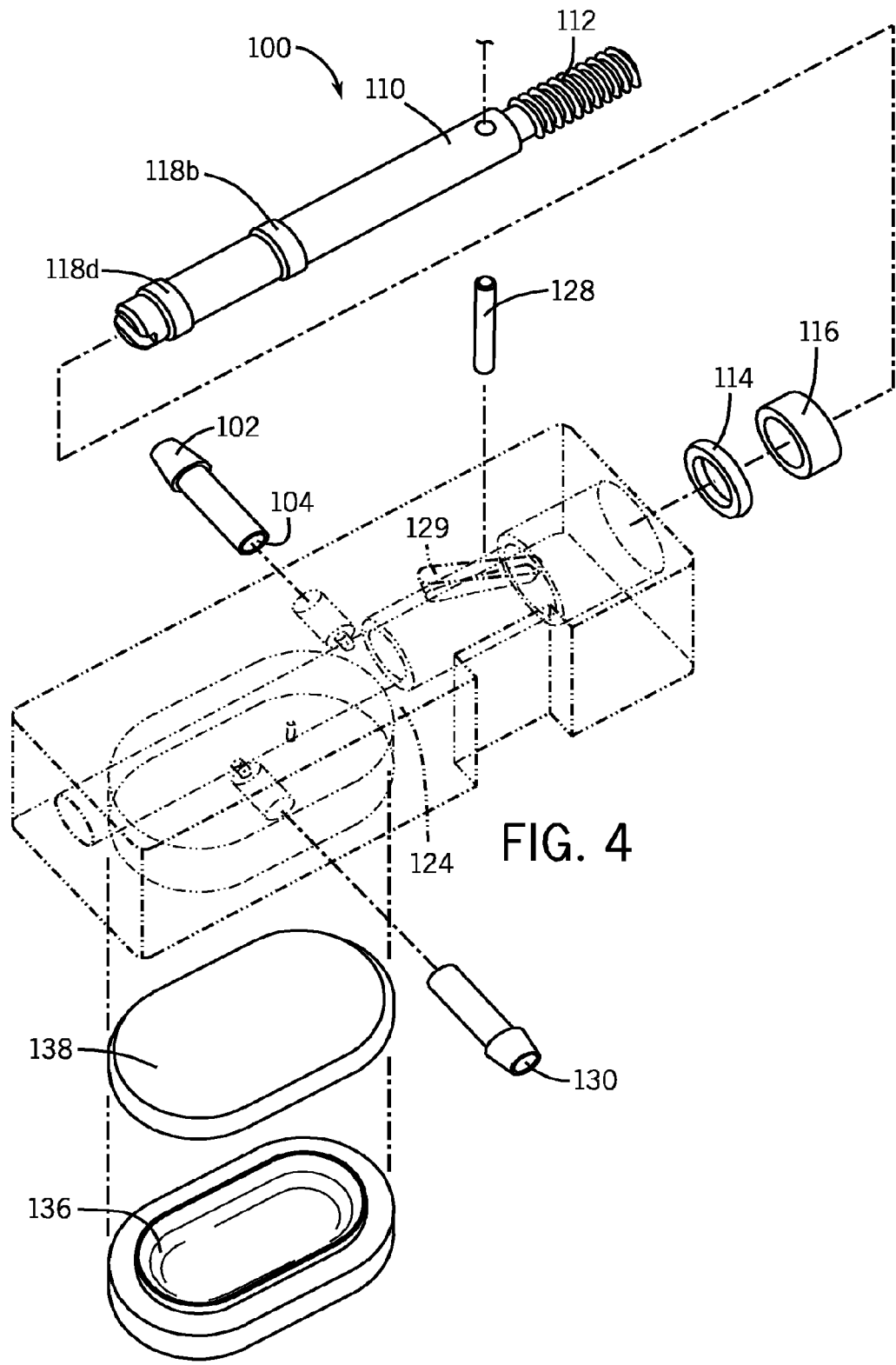
FIG. 4 is an exploded view of an embodiment of the flow metering device of the present disclosure having one chamber.
Figure 6:
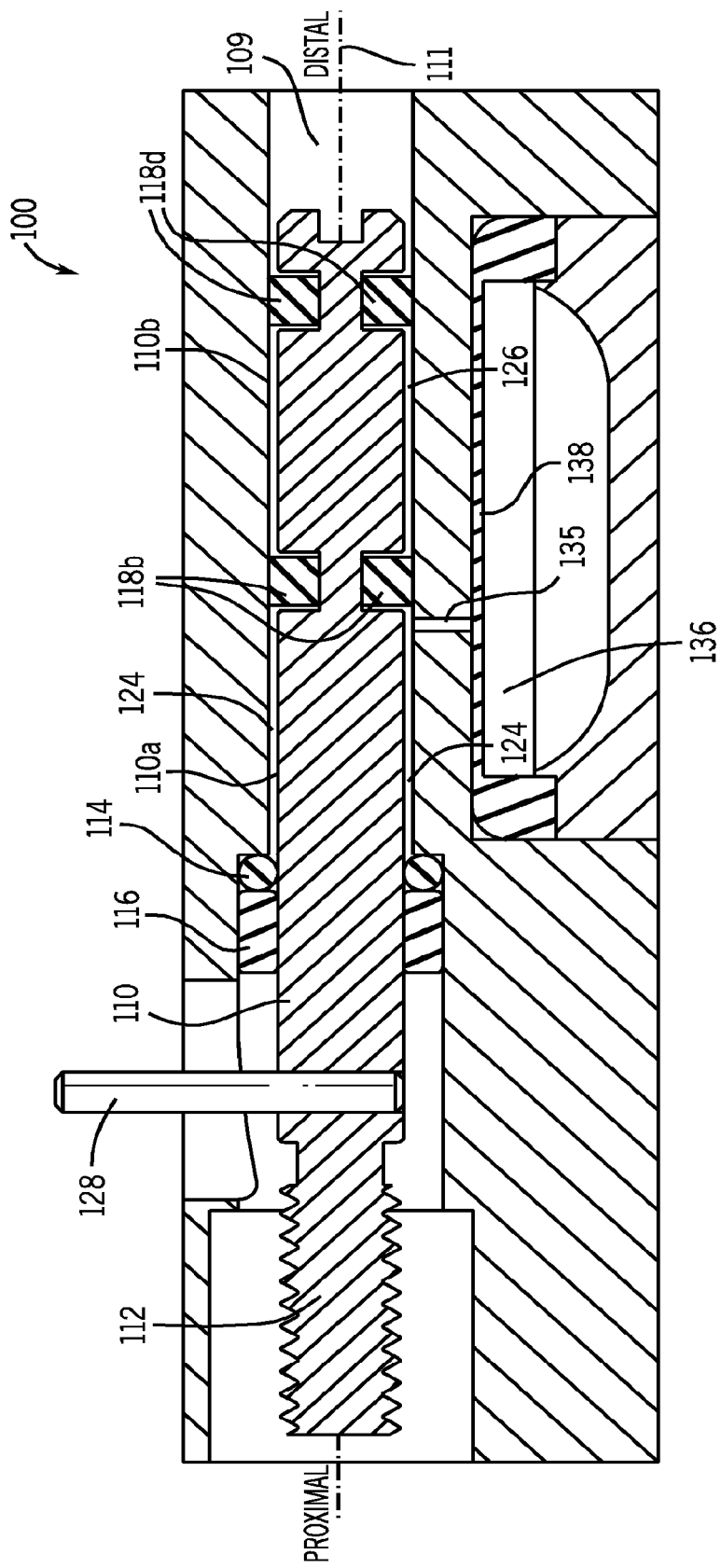
FIG. 6 is a cross-sectional side view of an embodiment of the flow metering device of the present disclosure having one chamber.

In other embodiments, devices of the present disclosure having only a single chamber are contemplated. As illustrated in FIGS. 2, 4, and 6, single chamber 136 associated with compressible member 138 is shown. Chamber conduit 135 allows chamber 136 to be in fluid communication with proximal flow space 124 and distal flow space 126. A shaft channel may be used in one-chamber embodiments.

As exemplified in FIG. 6, one-chamber versions of the devices of the present disclosure have two fixed seals 118b, 118d that are disposed along actuation shaft 110. Thus, two flow spaces are defined: proximal flow space 124, defined by actuation shaft seal 114, actuation shaft surface 110a, cavity wall 109a, and fixed seal 118b; and distal flow space 126, defined by fixed seals 118b and 118d, actuation shaft surface 110a, and cavity wall 109a. However, single chamber devices may also be designed with shaft channel 121 in actuation shaft 110, as described above.

According to embodiments, sensors 302 may be disposed within flow metering device 100, for example in the chambers 132, 136 below compressible members 134, 138 respectively (not shown), to measure pressure and thereby calculate the volume of fluid filling and dispensing from flow metering device 100. Generally, sensors 302 are disposed in a chamber of known volume with a fixed volume of fluid contacting the pressures sensors. Temperature sensors may be likewise disposed within flow metering device 100 to increase the accuracy of the calculations.

Flow metering device 100 may be disposable. Indeed, disposable devices comprising flow metering device 100 and flow material reservoir may be pre-charged with a flow material in flow material reservoir 300. The disposable device may be configured, for example, to integrally articulate with a reusable device that houses hardware such as user interfaces, sensor 302, actuator 202, and a microprossesor configured to operate flow metering device 100.

According to embodiments, flow material reservoir 300 may be designed to hold a flow material and a gas, with sensor 302 placed directly in flow material reservoir 300 as illustrated in the FIG. 1A. According to other embodiments, flow material reservoir 300 is separated from a gas chamber holding a sensor, as described variously in the patents and publications incorporated by reference herein.

Flow material reservoir 300 may be pre-filled with flow material. In other words, flow material reservoir 300 may be filled with a flow material as a step in the manufacturing process, or in a separate step after manufacturing, but before it is offered to users of the device. According to other embodiments, an end user of the flow metering device 100 fills the device with the flow material.

According to alternate embodiments, flow metering device 100 is a non-disposable, reusable device in which an attached flow material reservoir may be periodically refilled. Indeed, flow metering device 100 may be, for example, disposed downstream from source 300, such as a pump, and used as a flow rate regulator and safety device. As a flow rate regulator, it meters the rate at which flow material is delivered to a target because the input and output conduits are never in fluid communication simultaneously. As a safety device, if a pump or flow metering device 100 itself malfunctions, actuation shaft 110 is immediately arrested and the maximum additional flow material that can be delivered is the aliquot of flow material held in the chambers and spaces of flow metering device 100.

Figure 7:
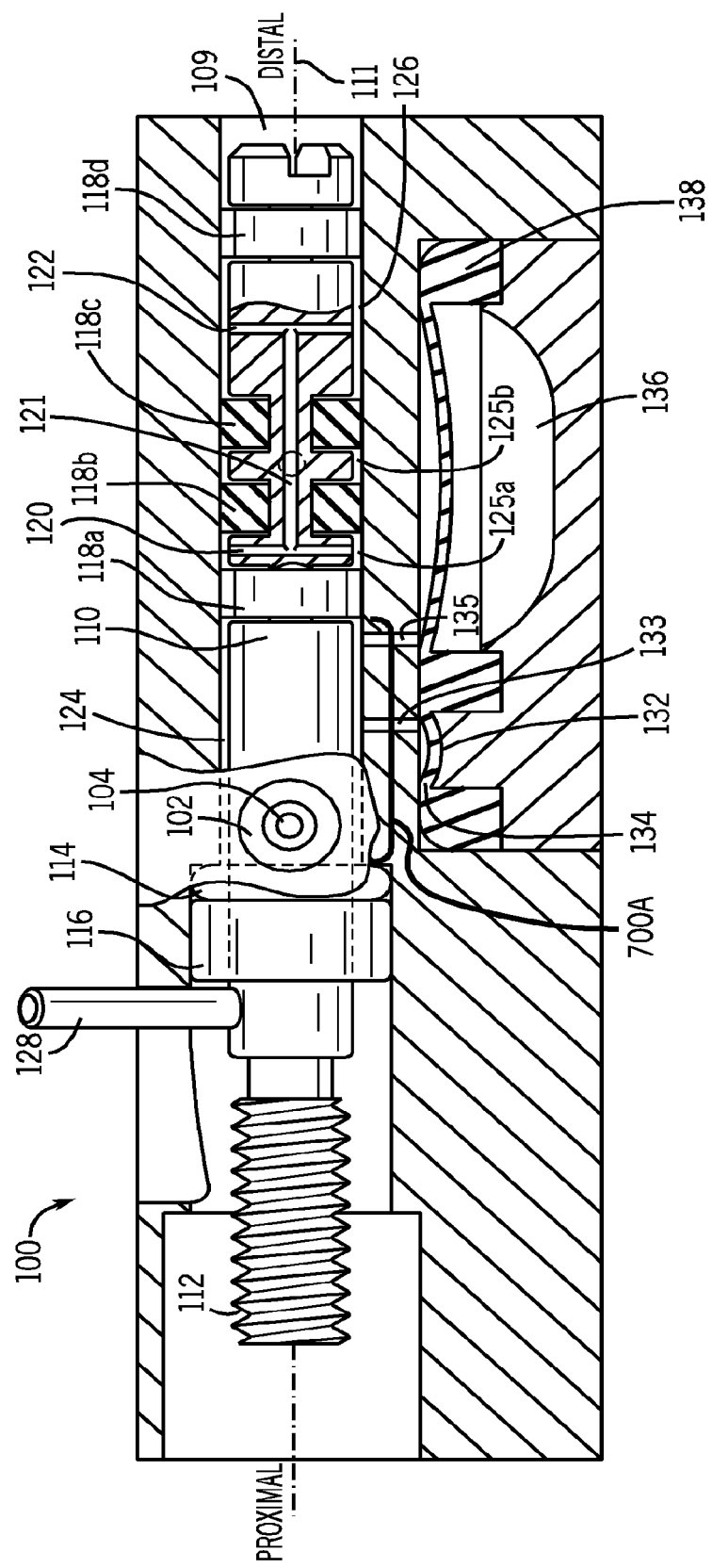
FIG. 7 is a cross-sectional side view of an embodiment of the flow metering device of the present disclosure having two chambers in a filling position.

The chambers in flow metering device 100 may be filled with a flow material when flow metering device 100 has actuation shaft 110 configured in a filling position, illustrated for a multichamber flow metering device 100 in FIG. 7. According to embodiments, the filling position occurs when the chambers, in this case first chamber 136 and second chamber 132 are in fluid communication with proximal flow space 124 via first chamber conduit 135 and second chamber conduit 133.

In the filling position, actuation shaft 110 is located so that fixed seal 118a is distal to first chamber conduit 135 and second chamber conduit 133. To accomplish this, actuation shaft 110 may be moved distally, thereby causing fixed seals 118a-118d to move distally with it. As illustrated in FIG. 7, once these components are in this position, actuation shaft connector 112 is in a distal position relative to its outer flow material dispense positions described below.

As actuation shaft 110 moves, actuation guide 128 imparts rotational motion to actuation shaft 110 around long axis 111 of actuation shaft 110; this causes moveable seals 118a-118d to rotate as well. A small degree of rotation reduces friction as actuation shaft 118a-118d moves distal and proximal in flow metering device cavity 109. Embodiments are expressly contemplated that do not have actuation guide 128 or actuation rotation channel 129, and therefore do not provide a rotational capability to actuation shaft 110 and seals 118a-118d. In the filling position depicted in FIG. 7, flow metering device 100 chambers 132, 136 may be filled with a fluid such as a flow material via input conduit 104 of input device 102 from, e.g., flow material reservoir 300 shown in FIG. 1A. When flow metering device 100 is in the filling position, first chamber 136 and second chamber 132 are in fluid communication with input conduit 104 via proximal flow space 124 and first chamber conduit 135 and second chamber conduit 133, respectively. According to embodiments and as shown in the Figs., e,g., FIG. 5, fluid contacts compressible members 138, 134, which distend into chambers 136, 132 respectively. According to other embodiments, fluid actually flows into each chamber and causes compression of compressible members within each chamber, for example closed-cell foam. The energy stored by the compressible members then cause the flow material to flow from the chambers to output conduit 130 and from the output conduit 130 to a target when actuation shaft 110 is in its dispense position(s).

In use, fluid such as flow material that is flowing into first chamber 136 and second chamber 132 may be pressurized. Thus, for example, as the flow material flows into each of first chamber 136 and second chamber 132, first compressible member 134 and second compressible member 134 are compressed, thereby storing the energy of the pressurized flow material when input conduit 104 is no longer in fluid communication with first chamber 136 and second chamber 132. Flow material may also enter unpressurized and compress compressible members 136, 134 as addition flow material is pumped into each chamber.

As illustrated by the embodiment shown in FIG. 7, compressible members 138, 134 may comprise an elastomeric membrane. As shown in FIG. 7 and related embodiments, flow material never actually enters chambers 136, 132, but rather contacts compressible members 138, 134, each of which distends into first chamber 136 and second chamber 132, respectively. According to other embodiments, however, flow material may directly enter the chambers and contact other compressible members within the chambers. For example, compressible members 138, 134 comprise a closed cell foam disposed in each chamber 136, 132. If compressible members 138, 134 are mechanical devices, each compressible member 138, 134 may be a piston.

Filling may be considered complete when the flow material pressure at the source (or at a pumping pressure) and at the compressible members 138, 134 come into equilibrium or near equilibrium. According to other embodiments, filling may be considered complete prior to such pressure reaching equilibrium when actuation shaft 110 is moved whereby input conduit 104 is no longer in fluid communication with first chamber 136 or second chamber 132. It is possible that the chambers 136, 132 are not filled with the same volume of flow material.

Figure 8:
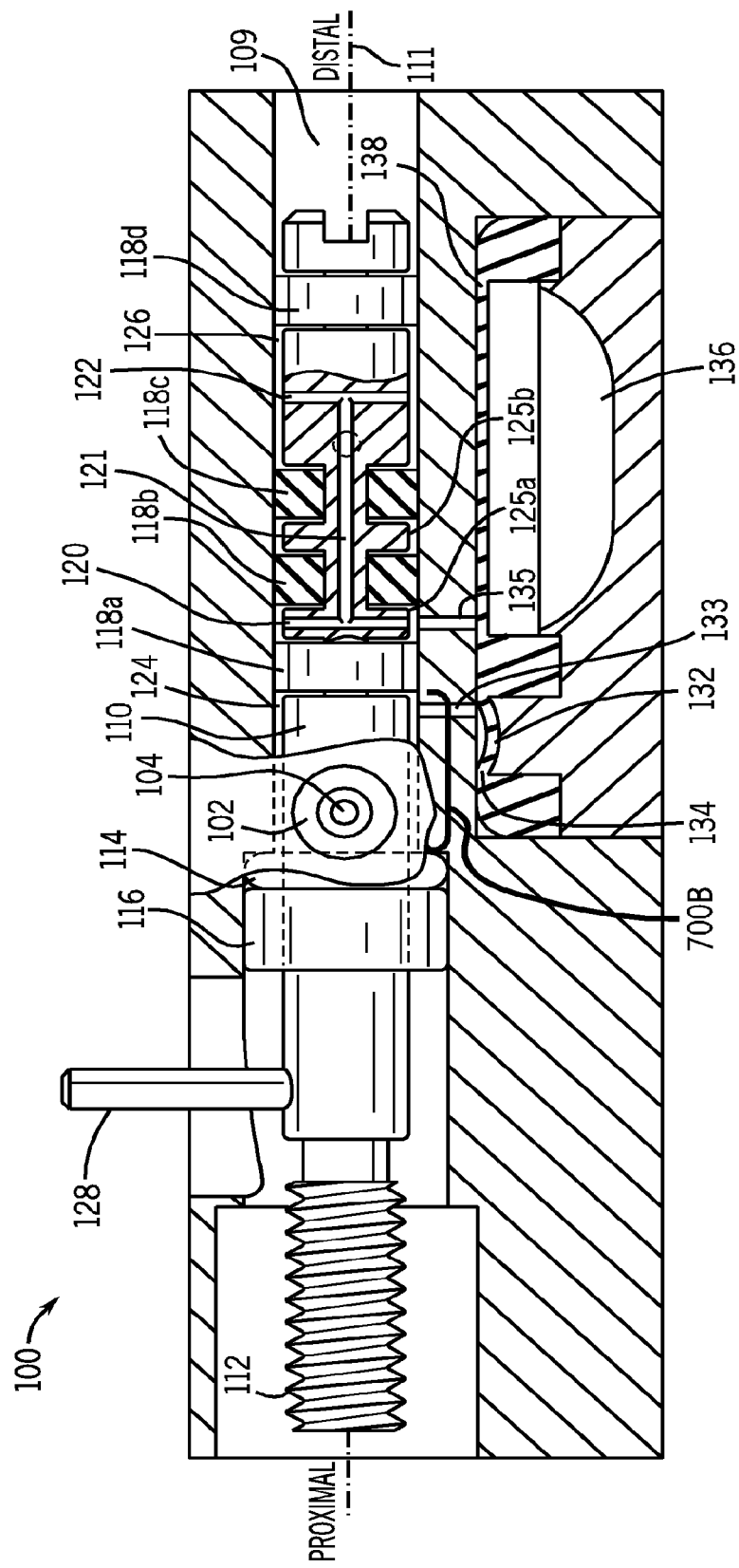
FIG. 8 is a cross-sectional side view of an embodiment of the flow metering device of the present disclosure having two chambers in a first dispense position.

As illustrated in FIG. 8, after first chamber 136 is filled to the desired volume, actuation shaft 110 is moved proximally to a first dispense position whereby first chamber 136 is no longer in fluid communication with input conduit 104. Note that in this position, second chamber 132 is still in fluid communication with input conduit 104, but second chamber 136 is not. Second chamber 132 remains in fluid communication with input conduit 104 via proximal flow space 124 and second chamber conduit 133. By varying any or a combination of the geometry, configuration, or number of fixed seals 118, embodiments are contemplated whereby no output of flow material occurs until both first chamber 136 and second chamber 132 are no longer in fluid communication with input conduit 104.

As shown according to the embodiment illustrated in FIG. 8, first chamber 136 is in fluid communication with output flow space 125 a via first chamber conduit 135. The energy stored in first compressible member 138 causes flow material to flow via conduit 135 into output flow space 125*a*, into shaft channel 121 via proximal shaft opening 120, and from shaft channel 121 through distal shaft opening 122 into distal flow space 126.

Distal flow space 126 comprises the space between actuation shaft 110 and the walls 109*a* of cavity 109 at the distal end of flow metering device 100. Distal flow space 126 is in fluid communication with output conduit 130, from which flow material is delivered to a target. Flow of flow material is effected via the energy stored in compressible member 138 to the target.

According to some embodiments, output conduit 130 (see FIGS. 1-2, for example) forms a conduit from connectors for connecting tubes, piping, or other flow facilitation devices. For example, in a medical context, output conduit 130 may comprise, in part, the conduit of a luer connector or hypodermic needle, according to exemplary embodiments.

According to embodiments of one chamber versions of flow metering device 100 (see FIGS. 2, 4, and 6, for example) and as disclosed above, shaft channel 121, proximal shaft opening 120, and distal shaft opening 122 are omitted. Thus, chamber 136 is either in fluid communication with input conduit 104 via proximal flow space 124, in fluid communication with output conduit 130 via distal flow space 126, or not in fluid communication with either proximal flow space 124 or distal flow space 126 when fixed seal covers chamber conduit 133. Embodiments of one chamber versions of flow metering device 100 having shaft channel 121 are, however, contemplated and would operate according to the principles of flow through shaft channel 121 disclosed above.

Figure 9:
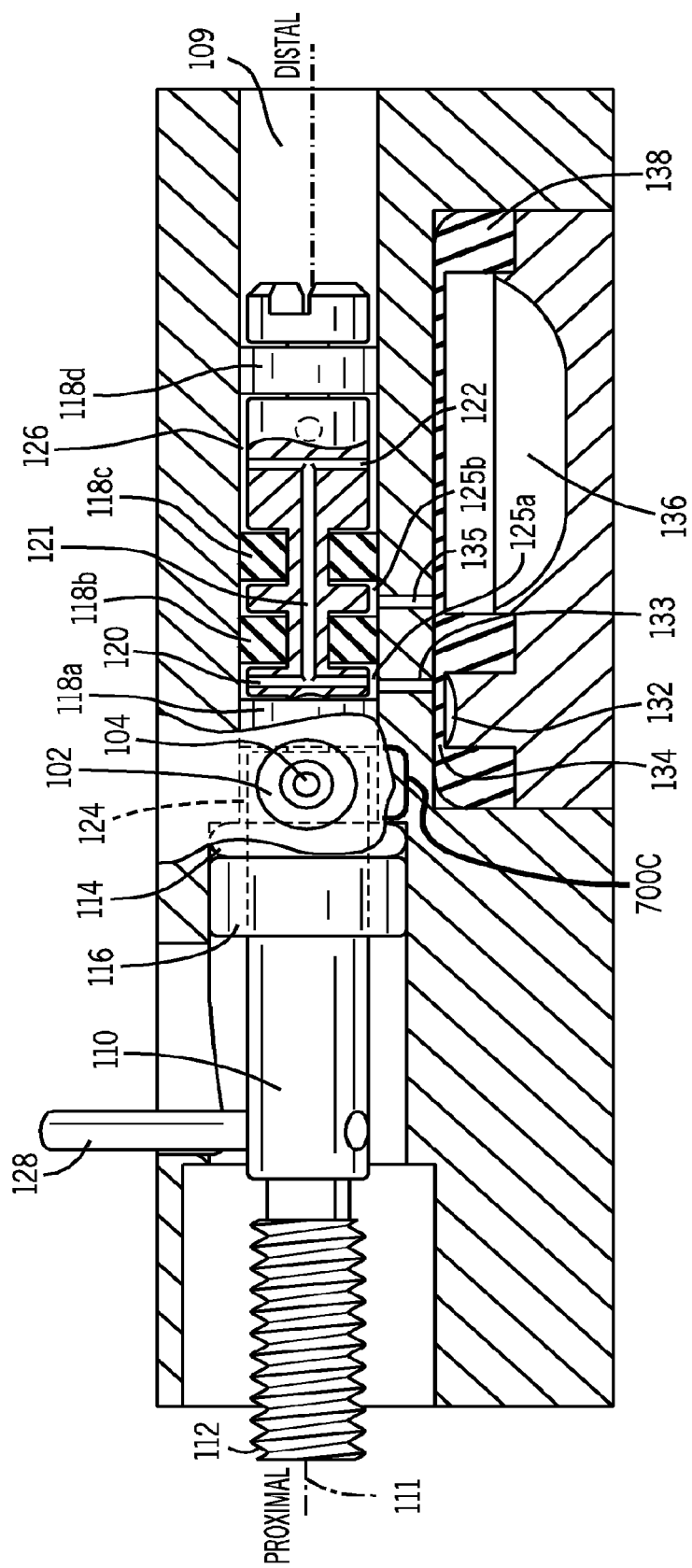
FIG. 9 is a cross-sectional side view of an embodiment of the flow metering device of the present disclosure having two chambers in a second dispense position.

Referring again to a two chamber embodiment of flow metering device 100 illustrated in, e.g., FIGS. 7-9, and referring specifically to the embodiment illustrated in FIG. 9 in which actuation shaft 110 has been moved fully proximal into a second dispense position. In this position, as illustrated, input conduit 104 is not in fluid communication with either of chambers 136, 132. As shown, second chamber 132 is in fluid communication with output conduit 130 via output flow space 125*a*, shaft channel 121, and distal flow space 124. First chamber 136 is in fluid communication only with sealed flow space 125*b* via first chamber conduit 135. As sealed flow space 125*b* is not in fluid communication with any other space or conduit, sealed flow space 125*b* prevents flow of the flow material contained in first chamber 136.

Various permutations may be made to any or a combination of the geometry, configuration or number, positioning or placement of fixed seals 118 along actuation shaft 110, as well as the positions of shaft channel 121, proximal shaft opening 120, and distal shaft opening 122 relative to the various positions of fixed seals 118 on actuation shaft 110. Indeed, configurations are possible whereby both first chamber 136 and second chamber 132 are in fluid communication with output conduit 130, where second chamber 132 is in fluid communication with output conduit 130 prior to first chamber 136 being in fluid communication with output conduit 130, and many other permutations depending on the configuration of the chambers, other components, and the objectives of the design.

According to embodiments, flow metering device 100 is a component of a disposable unit that works in conjunction with a reusable unit. For example, the disposable unit may comprise a flow material reservoir, and the components that comprise flow metering device 100. The reusable unit may comprise hardware and sensors used to determine the volume of flow material reservoir 300, including user interfaces and software for operating the device.

Operation of Flow Metering Device

According to embodiments of methods of the present disclosure, and as illustrated in FIG. 10, the two-chambered flow metering device 100 of, e.g., FIGS. 7-9 is operated by moving actuation shaft 110 proximally and distally to fill and dispense flow material in a controlled way. In operation 1002, actuation shaft 110 is positioned in a filling position (e.g., FIG. 7) whereby first chamber 136 and second chamber 132 are filled with a flow material in operation 1004. After filling, actuation shaft 110 is positioned in a first dispense position (e.g., FIG. 8) in operation 1006, whereby first chamber 136 dispenses flow material contained therein as previously described into output conduit 130 in operation 1008 thereafter to a target. Finally, in operation 1010, actuation shaft 110 is positioned in a second dispense position (e.g., FIG. 9). Flow material contained in second chamber 132 is dispensed as previously described into output conduit 130 in operation 1012 thereafter to a target.

Similarly, and as illustrated in FIG. 11, the operation of a one chamber embodiment of flow metering device 100 of, e.g., FIGS. 2, 4 and 6 is illustrated. In operation 1102, actuation shaft 110 is positioned in a filling position whereby chamber 136 is filled with a flow material in operation 1104. Once filled, actuation shaft 110 is positioned in a dispense position 1106 whereby flow material is dispensed as previously described into output conduit 130 in operation 1108 thereafter to a target.

Backstroke Volume

According to embodiments, for each complete fill-dispense cycle, actuation shaft 110 moves distally to fill and proximally to dispense flow material. Because input conduit 104 always remains in fluid communication with proximal flow space 124, and because proximal flow space 124 varies in volume according to the position of actuation shaft 110, as actuation shaft 110 moves to its dispense position (i.e., moves proximally), the volume of proximal flow space 124 is reduced, which subsequently forces some of the flow material remaining in proximal flow space 124 to return to flow material reservoir 300 via input conduit 104 in a predictable way. The volume of such flow material returning out of proximal flow space 124 is termed "backstroke volume." Because actuation shaft 110 is capable of moving to discrete positions at every cycle, the backstroke volume can be the same for each cycle. If the backstroke volume is known, then such volume can be used for a variety of calculations and advantages, including calculating, e.g., the volume of flow material reservoir 300 and to improve the safety of flow metering device 100 and devices used in conjunction with it.

Knowing a precise value of the backstroke volume provides a platform for accurately determining the volume of flow material reservoir 300 volume (or the volume of the fluid in flow material reservoir 300) and its flow rate by eliminating cumulative error that can occur from the use of prior determinations of the volume of flow material reservoir 300 or from calculation errors due to sensor drift or offset. Because the backstroke volume should be constant, if a backstroke volume is returned that is unexpected, the system may be configured to halt operations or generate an error or warning message.

Moreover, some sensors such as pressure transducers accumulate error over time due to sensor fatigue and other factors. Increasing error may be introduced, for example, by using values determined in prior measurements, each of which may have small measurement errors. When subsequent volume determinations are based on prior measured values which are in and of themselves inaccurate, each subsequent cycle potentially becomes increasingly inaccurate by coupling the error from prior measurements with sensor error in subsequent measurements. For example, when flow material reservoir 300 is nearly empty, repeated use of Boyle's law to determine the volume of flow material chamber 300 will result in reduced accuracy because small errors occurring in the measurement of each pressure measurement (beginning when flow material reservoir 300 was, for example, full of flow material) can accumulate over time. Use of a known backstroke volume, however, provides a novel method accurately to determine the volume of flow material reservoir 300 at any given cycle, thus minimizing cumulative error from prior cycles or from sensor drift/offset.

Moreover, according to embodiments, use of a known backstroke volume provides an additional safety mechanism. The devices of this disclosure can be used in various ways to improve safety: for example, the maximum size aliquot that can be inadvertently delivered in the event of a catastrophic failure is small because the metering methods described herein does not allow flow material reservoir 300 to be in fluid communication with the target. Second, by knowing an accurate backstroke volume, the cumulative error of the pressure sensors is eliminated, resulting in more accurate dosing of flow material. In addition, knowing the backstroke volume allows for constant and real-time monitoring of the mechanical components of device 100 to ensure their proper functioning (i.e., the volume of flow material returned to flow material reservoir 300 on each backstroke should be constant). If an unexpected backstroke volume is returned, the system can automatically shut down, be temporarily disabled, generate an error message, etc. to avoid the possibility of inaccurate dosing of flow material due to mechanical failure of the device. To avail oneself of these safety features, one or more flow metering devices such as those described herein may be disposed along the flow path so to meter flow of fluid such as flow material.

According to embodiments, the flow metering device 100 is disposed downstream from the pump. According to alternative embodiments, however, flow metering device 100 may be disposed upstream of a pump; the principles disclosed herein apply irrespective of whether flow material reservoir 300 is disposed upstream or downstream from the flow metering device.

Because actuation shaft 110 may be moved back and forth in cavity 109, each stroke (fill-dispense cycle) causes a quantity of flow material to be evacuated from or flow into the chambers and conduits of flow metering device 100. For example, when actuation shaft 110 is moved proximally, the volume of proximal flow space 124 is reduced and the excess flow material volume (backstroke volume) back flows into flow material reservoir 300. According to embodiments, if flow material reservoir 300 is disposed downstream of flow metering device 100, then proximal movement of actuation shaft 110 causes backstroke of flow material into cavity 109 (the backstroke volume is constant because its volume may be determined by fixed mechanical components; namely, actuation shaft 110, cavity 109, actuation shaft seal 114 and fixed seal 118a). The change in the volume of flow material reservoir 300 likewise can be measured. The following discussion assumes that flow material reservoir 300 is disposed upstream from flow metering device 100, but the principles described herein may be adapted by a person of ordinary skill in the art and implemented in the case where flow material reservoir 300 is disposed downstream from flow metering device 100.

As described above, the actuation shaft 110 of embodiments the flow metering device 100 may occupy at least two positions: a filling position for filling chambers 132, 136, and a dispense position for dispensing flow material from flow metering device 100. FIG. 7 illustrates actuation shaft 110 disposed in a fill position, where actuation shaft 110 is positioned distally, as described above. In this position, flow material may be transferred through input conduit 104 and proximal flow space 124 into at least one of first chamber 136 and second chamber 132 via first and second chamber conduits 135, 133, respectively. In so doing, proximal flow space 124 is likewise charged with flow material. The volume of proximal flow space 124 at this point is denoted by the length 700A in FIG. 7.

In FIG. 8, actuation shaft 110 is positioned into a first dispense position by positioning actuation shaft proximally. Thus, the length 700A becomes length 700B. As second chamber 132 is already filled, the volume of flow material that was in proximal flow space 124 (represented in the view of FIG. 8 by the difference in length between length 700A and length 700B) is removed through input conduit 104 and into flow material reservoir 300 due to an increase in pressure of the flow material in proximal flow space 124. The volume of this removed flow material (backstroke volume) is known, as it can be derived mathematically or by an initial measurement. The same principle operates whether actuation shaft is positioned in the first dispense position illustrated in FIG. 8 (length 700B) or the second dispense position illustrated in FIG. 9 (length 700C).

Figure 12:
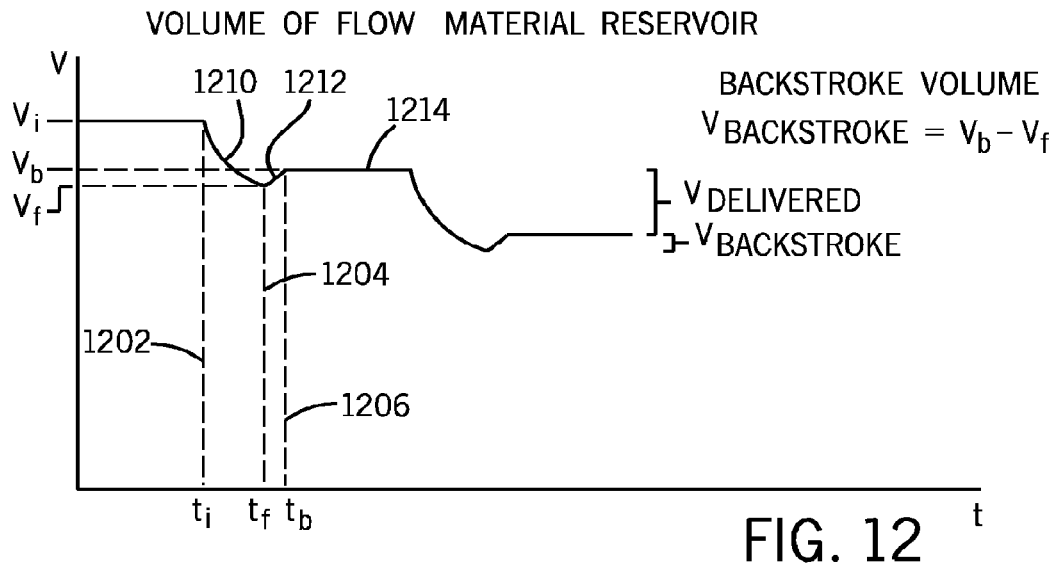
FIG. 12 is a graph of embodiments for flow volume data over time illustrating the phenomena as an actuation shaft is moved.

FIG. 12 is a schematic illustrating the relative volume of fluid such as flow material present in flow material reservoir 300 as a function of time when a pump is used in conjunction with the devices of the present disclosure. At time $t_i$ (dashed line 1202), actuation shaft 110 is positioned in a charge or filling position (operation 1302 of FIG. 13) and an initial known volume $V_i$ of flow material is present in reservoir 300. Next, flow material flows from flow material reservoir 300 into at least one chamber 132, 136 in flow metering device 100 as shown by solid line segment 1210. At the end of this chamber filling process, indicated in FIG. 12 as time $t_f$ (dashed line 1204), the volume $V_f$ of flow material remaining in reservoir 300 before the backstroke is measured or determined in operation 1304 of FIG. 13.

Figure 13:
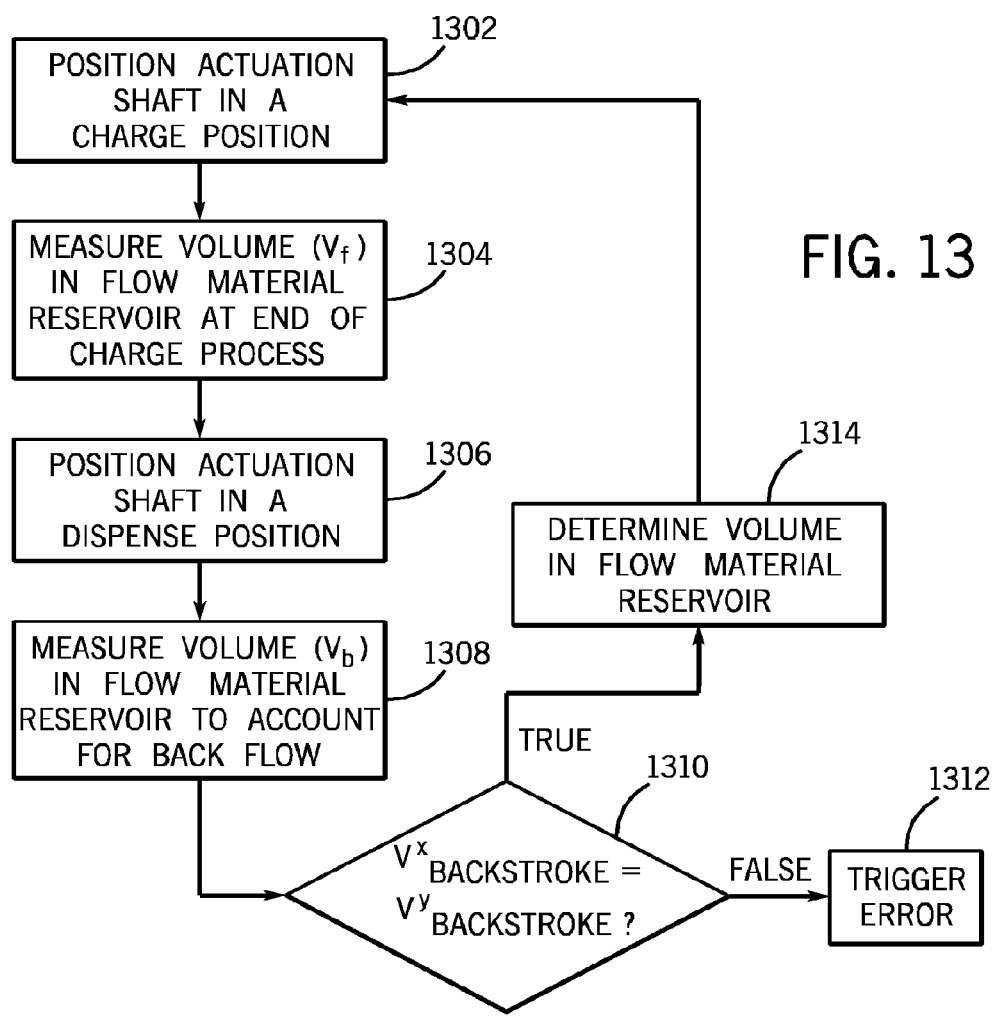
FIG. 13 is a flow diagram of embodiments of a method for calculating the volume of a flow material reservoir after a known aliquot is flowed into the reservoir by action of movement of an actuation shaft.

At time $t_b$ (dashed line 1206), actuation shaft 110 has been positioned into a dispense position (operation 1306 of FIG. 13). Because actuation shaft 110 has moved proximally between time $t_f$ and time $t_b$, (i.e., the "backstroke") and the volume in proximal flow space 124 is reduced, flow material returns through input conduit 104 and ultimately back into flow material reservoir 300 (illustrated by line segment 1212 in FIG. 12). At the end of the period in which the system has been receiving this backstroke material into flow material reservoir 300 (time $t_b$), the volume $V_b$ of flow material residing in flow material reservoir 300 is determined in operation 1308. The backstroke volume ($V_{backstroke}$) may be calculated as the difference between $V_b$ and $V_f$.

$$V_{backstroke} = V_b - V_f \tag{1}$$

After time $t_f$, no further appreciable backstroke volume is observed and the volume $V_b$ of flow material in reservoir 300 remains relatively constant until actuation shaft 110 is repositioned back to a fill position. The interim time period after the backstroke but before the actuation shaft 110 is moved to its fill position is represented as line segment 1214. The point along the line where the next drop in volume occurs represents the next fill-dispense cycle.

Device Integrity Using Backstroke Volume

Because the backstroke volume is approximately constant, the backstroke volume measured on each fill-dispense cycle should be the same $V_{backstroke}^x = V_{backstroke}^y$ for any two arbitrary times x and y, as shown in operation 1310 of FIG. 13.

By measuring the volume of flow material reservoir 300 immediately prior to repositioning of actuation shaft 110 to a dispense position (time $t_f$; dashed line 1204 of FIG. 12) and after the backstroke has stopped (time $t_b$; dashed line 1206 of FIG. 12), the integrity of the devices may be monitored on a continuous or semi-continuous basis. If a backstroke volume is determined to be significantly different (within a predetermined tolerance level) from the known backstroke volume expected or observed in prior fill-dispense cycles, then an error state can be triggered or initiated in operation 1312 of FIG. 13.

In operation 1314, if the backstroke volume is determined to be the same (within a predetermined tolerance level) from the volume expected or observed in prior fill-dispense cycles, the known backstroke volume is used to accurately determine the amount of flow material in flow material reservoir 300. Determination of the volume of reservoir 300 in this way eliminates much of the error observed by measuring the difference in volume calculated on each cycle. Because the backstroke volume is known and relatively constant over time, it can be used to more accurately measure volume in flow material reservoir 300.

Backstroke Volume Determination

To make use of the backstroke volume, the backstroke volume must initially be determined. To determine the backstroke volume initially, data from a sensor such as sensor 302 is obtained in an initialization procedure. To initially determine the backstroke volume, a complete initial fill-dispense cycle of flow metering device is performed (i.e., 1202 to 1206 in FIG. 12). The complete cycle can be performed prior to filling flow material reservoir 300 with a flow material (using, for example, a gas that is held in flow material reservoir 300) or performed after flow material reservoir 300 is filled with a flow material. In either case, the total initial volume of fluid in flow material reservoir 300 or the volume of flow material reservoir 300 must be known.

According to some embodiments, flow material reservoir 300 of known volume is disposed in a disposable chamber that is slightly pressurized and is in fluid communication with a pressure transducer. Initially, flow material reservoir 300 is empty (i.e., empty of flow material, but filled with another fluid, such as a slightly pressurized gas). In this state, the total volume of flow material reservoir 300 is known, but the backstroke volume is unknown. Therefore, prior to filling flow material reservoir 300 with flow material, a complete fill-dispense cycle is performed. Gas from the flow reservoir 300 flows into the chambers of flow metering device 100, which effects changes in pressure in flow material reservoir 300. The changes in pressure from a known configuration of volume and pressure is used to calculated the backstroke volume initially.

According to alternate embodiments, flow material reservoir 300 is filled with a flow material of a known volume. The process for determining the backstroke volume is performed exactly the same way, i.e., running one or more fill-dispense cycles.

Once the backstroke volume is known, it can be used to calculate the volume of flow material dispensed during each fill-dispense cycle, as disclosed herein.

Example 1

Using the Backstroke Volume to Determine the Flow Material Reservoir Volume

The backstroke volume can be used accurately to measure the volume of flow material reservoir 300 using Boyle's law. The principles outlined below are based on use of Boyle's law with the assumption that temperature is constant. Increased accuracy is possible with the use of temperature sensors.

According to some embodiments, flow material reservoir is part of a pump having a fluid chamber with a known volume of flow material therein and a gas chamber having a sensor disposed within it. The total volume of fluid chamber and gas chamber is fixed and known. When the volume of the gas chamber changes, the volume of the fluid chamber likewise changes in inverse proportional thereto (i.e., as the volume of the fluid chamber decreases, the volume of the gas chamber increases by the same amount). The gas chamber is sealed and has a sensor, for example a pressure transducer or temperature transducer, disposed therein.

According to alternative embodiments, flow material reservoir may comprise an integral chamber having a gas, a sensor, and flow material. According to this example, flow material reservoir is disposed upstream of flow metering device 100.

Flow material reservoir may be filled with fluid such as flow material, by the user. According to other embodiments, flow material reservoir is prefilled (for example, in the case where flow material reservoir is part of a disposable unit). According to embodiments, the flow material reservoir may be designed so that the volume of flow material reservoir 300 is known with accuracy either before, during, or after flow material has been dispensed.

Initialization (Determination of Backstroke Volume)

The backstroke volume must be determined if it is to be used to determine the volume of flow material reservoir 300 in each fill-dispense cycle. According to other embodiments, the backstroke volume may be known because flow metering device 100 is manufactured such that the backstroke volume is accurately determinable to some tolerable error level, according to embodiments.

According to other embodiments, flow metering device 100 is initialized to determine the backstroke volume. To do so, flow material reservoir 300 contains a fluid, for example, a pressurized gas or flow material. The total volume of flow material reservoir 300 must be known or the volume of flow material in reservoir 300 must be known.

According to embodiments, the backstroke volume may be calculated using the sensor(s). The pressure of flow material reservoir 300 is measured. Let $V_i$ designate the volume of flow material reservoir 300 at this point (see FIG. 12, time $t_i$). Actuation shaft 110 is then moved to its filling position. In this position, fluid flows from flow material reservoir 300 flows into chambers 132, 136 via proximal flow space 124 of flow metering device 100. Let the volume of flow material reservoir 300 after chambers of flow metering device are filled with fluid from the flow material reservoir 300 be designated $V_f$ (see FIG. 12, time $t_f$). Finally, actuation shaft 110 is moved to its dispense position. This movement causes a backstroke volume of fluid to into flow material reservoir 300. At the end of this process, the volume of flow material reservoir 300 is designed as $V_b$ (see FIG. 12, time $t_b$). Because the initial volume of flow material reservoir 300 was known, $V_f$ and $V_b$ may be determined by the following equations:

$$V_f = \frac{P_i V_i}{P_f} \qquad (2a) \text{ and } (2b)$$

and $$V_b = \frac{P_i V_i}{P_b},$$

where $P_i$, $P_f$, and $P_b$ are the measured pressure in the flow material reservoir 300 at the respective times $t_i$, $t_f$, and $t_b$. The backstroke volume is the difference between $V_b$ and $V_f$. Thus, the volume of fluid returned to flow material reservoir 300 after the backstroke, and therefore the backstroke volume, can be calculated by:

$$V_{backstroke} = \frac{P_i V_i}{P_b} - \frac{P_i V_i}{P_f}. \qquad (3)$$

The initialization procedure may be repeated a number of times and the $V_{backstroke}$ values calculated from each initialization procedure may be averaged or otherwise used to obtain an acceptable value for $V_{backstroke}$.

It should be noted that in all cases the volume to be measured is the volume of the fluid in flow material reservoir 300. In certain cases, the volume of the fluid in flow material reservoir 300 is substantially the same as the volume of flow material reservoir 300. In either case, it is the change in volume, not the absolute volume that is used to determine the backstroke volume and the volume dispensed during each fill-dispense cycle. For each fill-dispense cycle, the change in volume of flow material reservoir or the fluid in flow material reservoir changes by the same amount. By observing the changes in volume, as well as knowing the initial volume of flow material in flow material reservoir 300, the volume of flow material dispensed from flow metering device 100 can be substantially precisely determined.

According to some embodiments, the sensor directly measures the fluid volume in flow material reservoir 300, for example via acoustic or other similar methods of volume determination disclosed herein or incorporated by reference herein. In other embodiments, the sensor(s) are disposed in separate chambers, for example gas chambers, and the volume of the fluid/flow material reservoir 300 are inferred because the total volume of the chamber and the flow material reservoir is fixed (i.e., the volume of the gas chamber is determined, which allows for determination of flow material reservoir by subtracting the volume of the gas chamber from the total, fixed volume of the flow material reservoir plus the gas chamber). Thus, the terms can be used interchangeably without taking away from the general principles for determining the backstroke volume and subsequent volumes for fluid or flow material dispensed from flow metering device 100.

Calculation of Absolute Volume of Flow Material Reservoir

Once the backstroke volume ($V_{backstroke}$) is known, it can be used to determine the volume of flow material reservoir 300 after each fill-dispense cycle. By calculating the difference in the volume of flow material reservoir 300 after each fill-dispense cycle from the volume of flow material reservoir 300 in the prior cycle, the precise volume of the aliquot metered to a target from flow material reservoir 300 via flow metering device 100 may be determined. Moreover, if the backstroke volumes for each fill-dispense cycle are not within a predetermined tolerance level, a mechanical breakdown may be more likely to have occurred and an error state may be initiated.

According to embodiments, to determine the absolute volume of flow material reservoir 300 at the end of each cycle (line 1206 in FIG. 12, time $t_b$), the backstroke volume ($V_{backstroke}$) may be used. Simplifying equation (3) and solving for $P_i V_i$ yields the equation:

$$P_i V_i = \frac{V_{backstroke} P_b P_f}{P_f - P_b}. \qquad (4)$$

To solve for $V_b$ (which is the volume of flow material reservoir 300 at the end of each cycle while actuation shaft 110 is in its dispense position), equation 2b is solved:

$$V_b = \frac{P_i V_i}{P_b}. \qquad (2b)$$

Because $P_i V_i$ was previously solved in equation 4, $V_b$ can be determined using only the backstroke volume by substitution:

$$V_b = \frac{V_{backstroke} P_f}{(P_f - P_b)}. \qquad (5)$$

Thus, for any given cycle, the volume of flow material reservoir 300 ($V_b$) is determined. Note that $V_b$ from the previous cycle becomes $V_i$ for the current cycle.

Calculation of Delivered Aliquot Size

To determine the volume delivered from flow metering device 100 during any given cycle (i), the following equation is used:

$$V_{delivered}{}^i = V_b{}^{i-1} - V_b{}^i. \qquad (6)$$

Notably, when $V_{backstroke}$ is measured initially, sensor drift becomes less relevant because all of the pressure measurement from which $V_b$ is calculated occur within a very small window in which overall drift is negligible. Consequently, the problem of cumulative error due to sensor drift is reduced.

Example 2

Sensor Offset Calibration Using the Backstroke Volume

At certain times, if the volume of flow material reservoir 300 and the backstroke volume are known, sensor offset calibration may be accomplished. Some sensors, such as pressure transducers, tend to lose accuracy over time due to mechanical fatigue and other factors. For example, pressure transducers work by measuring the deflection of a strain gauge. The strain gauges tend to plastically deform over time, making them less accurate. Moreover, when measuring greatly different pressures, the strain gauges behave slightly differently, which also introduces error, especially when volume of flow material reservoir 300 is calculated from initial measurements when flow material reservoir 300 is full and later measurements when flow material reservoir 300 is empty. The deflection affects the measured voltage, which can be expressed as a line correlating pressure and voltage.

Deformation of the strain gauge affects pressure measurements in two ways: the slope of the line comparing voltage to pressure can change (drift) and the y-intercept of the line can change (offset).

As discussed above, use of the backstroke volume to calculate the absolute volume of flow material reservoir 300 greatly diminishes the effect of drift. However, it is believed that use of the backstroke volume to calculate the absolute volume of flow material reservoir 300 does not affect or increases potential error due to changes in the offset. Thus, a method of periodically calculating and adjusting the offset is presented.

According to embodiments, to calculate the offset, the volume of flow material reservoir 300 must be known at some point in the process with relative accuracy independent of calculating it using sensor 302 data. For example, prior to filling flow material reservoir 300 with flow material, its volume may be accurately known. Alternately, the volume of a pre-filled flow material reservoir 300 may be known. In another alternative, the volume of flow material reservoir 300 will be known with sufficient accuracy at given points in the fill-dispense cycle, for example when all flow material has been dispensed from reservoir 300.

Turning again to FIG. 12, when flow material chamber is empty or holds a known volume prior to a backstroke, the point in each stroke cycle will correspond to line 1204. Using the known backstroke volume and the known volume of flow material reservoir 300, the offset can be calculated using Boyle's law between lines 1204 and 1206, the difference in volume of which corresponds to $V_{backstroke}$. The offset for each pressure measurement can be expressed as the measured pressure P plus an offset value $P_{offset}$. If sensor 302 is perfectly calibrated, the offset value will be zero.

Thus:

$$P_b V_b = P_f V_f \qquad (7).$$

Substituting pressure value to include the updated pressure offset yields:

$$(P_b + P_{offset})(V_f + V_{backstroke}) = (P_f + P_{offset}) V_f \qquad (8)$$

Note that the volume $V_b$ is expressed on the left side of the equation is expressed in terms of $V_f$, namely:

$$V_b = V_f + V_{backstroke}. \qquad (1)$$

Solving for $P_{offset}$ yields the equation:

$$P_{offset} = \frac{P_f V_f - P_b V_f - P_b V_{backstroke}}{V_{backstroke}}. \qquad (9)$$

Thus, $P_{offset}$ can be derived if the volume of flow material reservoir 300 ($V_f$) is known and the backstroke volume ($V_{backstroke}$) is known.

Example 3

Use of Flow Metering Device to Dispense Insulin from an Integrated Insulin Pump and Flow Metering Device Flow metering device 100 is useful in the dispensing of insulin as the flow material. Flow metering device is disposed as part of an integrated infusion pump, such as those incorporated by reference herein, or can pump insulin straight from the insulin reservoir as disclosed herein. According to some embodiments, flow material reservoir 300 is disposed upstream from flow metering device 100. Flow material reservoir 300 contains a pressure sensor and a temperature sensor for measuring the pressure and temperature in the insulin chamber, respectively. According to other embodiments, flow material reservoir comprises a bag or other collapsible member disposed in a chamber that can hold a pressurized gas and that also houses the sensors.

Prior to using the insulin pump to dispense insulin, the backstroke volume must be determined. As disclosed above, backstroke volume may be determined when the insulin reservoir is full of insulin, or when it holds another fluid, such as a slightly pressurized gas.

When the insulin reservoir is full of insulin when the initialization is performed, a user initializes the pump by running one or more fill-dispense cycles with the pressurized gas to establish the backstroke volume. Once the backstroke volume is determined, the user connects the insulin pump for actual delivery of insulin into the blood stream.

Alternately, the user initializes the insulin pump prior to filling the insulin reservoir with insulin. Rather than performing fill-dispense cycles with insulin, it is performed with a fluid being held in the flow material reservoir, such as a pressurized gas. After the backstroke volume has been determined, the user fills the insulin pump with a quantity of insulin and puts the pump into fluid communication with the blood stream. Thereafter, each fill-dispense cycle will dispense an aliquot of insulin to a user.

Thereafter, the insulin pump metering insulin to a patient as described herein. In multiple chamber versions, bolus volumes of insulin can be delivered, for example by dispensing for the larger chamber in the flow metering device as disclosed herein. Likewise, basal doses may be delivered by repeatedly filling and dispensing from the smaller chamber of flow metering device, depending on the configuration of the chamber in the flow metering device and the flow paths defined therein.

Example 4

Use of Flow Metering Device to Dispense Insulin from a Disposable Insulin Reservoir Cartridge and Flow Metering Device According to some embodiments, flow metering device is part of a disposable cartridge. The disposable cartridge contains the insulin (flow material) reservoir and the flow metering device. The disposable cartridge is adapted to mateably fit into a reusable device that houses the hardware, user interface, and pressure and temperature sensors. By mating the disposable cartridge and the reusable device, the sensors may be placed into fluid communication with the flow material reservoir.

According to embodiments, the sensors of the reusable device are disposed in a separate gas chamber designed to change in volume as the flow material reservoir changes in volume. For example, the insulin reservoir may comprise a bag of insulin that is placed in a pressurizable chamber. As insulin is dispensed, the volume of the bag is reduced, whereby the volume of the chamber housing the bag is increased by the same amount. In some embodiments, the disposable contains both the insulin bag (flow material reservoir) and the chamber that houses the bag. When mated to the resusable device, the chamber holding the bag is sealably placed into fluid communication with the sensors.

Once the disposable cartridge and the reusable device are mated together, the initialization procedure must be performed to determine the backstroke volume as described above. The volume of insulin in the insulin reservoir will be known prior to performing the initialization procedure. Accordingly, a small volume of insulin is dispensed during the initialization procedure, rather than quantities of pressurized gas as described above.

Thereafter the mated disposable cartridge and reusable device dispenses insulin as described above.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A flow metering system, comprising:
   a cavity;
   an actuation shaft disposed in the cavity and movable between a first position within the cavity and a second position within the cavity;
   an input conduit fluidly connectable to a flow material reservoir, the input conduit in fluid communication with a proximal flow space defined by the cavity when the actuation shaft is in both the first position and the second position;
   a flow metering device chamber in fluid communication with the input conduit through the proximal flow space when the actuation shaft is in the first position for filling the flow metering device chamber with flow material from the flow material reservoir and not in fluid communication with the input conduit when the actuation shaft is in the second position;
   an output conduit adapted to dispense flow material from the flow metering device chamber when the actuation shaft is in the second position; and
   a sensor adapted to obtain data for determining a backstroke volume of flow material from the proximal flow space into the flow material reservoir when the actuation shaft is moved from the first position that fills the flow metering device chamber with flow material to the second position that dispenses the flow material from the flow metering device chamber through the output conduit.

2. The flow metering system of claim 1, wherein the flow material reservoir comprises a first chamber holding the flow material and a second chamber holding a gas and the sensor.

3. The flow metering system of claim 1, wherein the sensor is a pressure sensor.

4. The flow metering system of claim 1, further comprising a pump that houses the flow material reservoir and the sensor.

5. The flow metering system of claim 4, wherein the pump includes a user interface and a processor adapted to control movement of the actuation shaft and determine the change in volume based on the data acquired by the sensor.

6. The flow metering system of claim 5, wherein the processor is adapted to control the sensor to acquire data before positioning the actuation shaft in the second position and after positioning the actuation shaft in the second position.

7. The flow metering system of claim 5, wherein the processor is adapted to determine the difference between a volume of the flow material in the flow material reservoir before positioning the actuation shaft in the second position and a volume of the flow material in the flow material reservoir after positioning the actuation shaft in the second position.

8. The flow metering system of claim 5, wherein the processor is adapted to determine the backstroke volume from the data acquired by the sensor each time the actuation shaft is moved from the first position to the second position, and wherein the processor is adapted to stop movement of the actuation shaft if a first determined backstroke volume is not substantially the same as a second backstroke volume.

9. The flow metering system of claim 5, wherein the processor is adapted to determine the backstroke volume from the data acquired by the sensor each time the actuation shaft is moved from the first position to the second position, and wherein the processor is adapted to indicate an error state on the user interface if a first determined backstroke volume is not about equal to a second backstroke volume.

10. A flow metering system, comprising:
    a cavity defining a proximal flow space;
    an actuation shaft disposed in the cavity;
    a flow metering device chamber;
    a sensor; and
    a computer processor, the computer processor adapted to:
       position the actuation shaft in a first position in the cavity such that the flow metering device chamber is in fluid communication with the cavity;
       cause an aliquot of flow material to flow into the flow metering device chamber from a flow material reservoir through an input conduit and the proximal flow space;
       position the actuation shaft in a second position in the cavity to dispense the flow material from the flow metering device chamber out an output conduit with the flow material reservoir in fluid communication with the proximal flow space such that positioning of the actuation shaft to the second position causes a backstroke volume of flow material to flow from the proximal flow space into the flow material reservoir;
       observe a change in volume of the flow material in the flow material reservoir after the actuation shaft is moved to the second position with data gathered from the sensor; and
       determine the backstroke volume from the data.

11. The flow metering system of claim 10, where the processor is adapted to gather data with the sensor before positioning the actuation shaft in the second position and after positioning the actuation shaft in the second position.

12. The flow metering system of claim 10, wherein the processor is adapted to determine the backstroke volume by measuring a difference of a volume of flow material in the flow material reservoir before positioning the actuation shaft in the second position and a volume of the flow material in the flow material reservoir after positioning the actuation shaft in the second position.

13. The flow metering system of claim 10, further comprising the flow material reservoir, the flow material reservoir comprising a first chamber holding the flow material and a second chamber holding a gas and the sensor.

14. The flow metering system of claim 10, wherein the sensor is a pressure sensor.

15. The flow metering system of claim 10, wherein the processor is further adapted to stop actuation of the actuation shaft if a first determined backstroke volume is not substantially the same as a second backstroke volume.

16. The flow metering system of claim 10, wherein the processor is further adapted to trigger an error state if a first determined backstroke volume is not about equal to a second backstroke volume.

17. The flow metering system of claim 10, further comprising a pump that houses the flow material reservoir and the sensor.

\* \* \* \* \*

UNITED STATES PATENT AND TRADEMARK OFFICE
CERTIFICATE OF CORRECTION

PATENT NO.        : 9,250,106 B2
APPLICATION NO.   : 14/070879
DATED             : February 2, 2016
INVENTOR(S)       : Rosinko et al.

Page 1 of 1

It is certified that error appears in the above-identified patent and that said Letters Patent is hereby corrected as shown below:

In the Specification

Column 3, lines 41-42:
Delete "According to embodiments"

Column 13, line 13:
Delete "$V_{backstroke}x = V_{backstroke}y$" and insert -- $V^{x}_{backstroke} = V^{y}_{backstroke}$ --

Column 16, line 43:
Delete "$V_{delivered}{}^{i}$" and insert -- $V^{i}_{delivered}$ --

Signed and Sealed this
Fourteenth Day of June, 2016

Michelle K. Lee
*Director of the United States Patent and Trademark Office*